United States Patent [19]
Niederauer et al.

[11] Patent Number: 5,904,658
[45] Date of Patent: May 18, 1999

[54] HAND-HELD MATERIALS TESTER

[75] Inventors: Mark Q. Niederauer; Robert P. Wilkes; George M. Niederauer; Sabine Cristante, all of San Antonio; Steven F. Cline, Austin; Robert A. Tynmann, San Antonio, all of Tex.

[73] Assignee: OsteoBiologics, Inc., San Antonio, Tex.

[21] Appl. No.: 08/916,277

[22] Filed: Aug. 22, 1997

Related U.S. Application Data

[60] Provisional application No. 60/024,527, Aug. 23, 1996.

[51] Int. Cl.$^6$ .................................................. A61B 5/103
[52] U.S. Cl. ............................................................ 600/587
[58] Field of Search .................................. 600/553, 587, 600/595; 73/81

[56] References Cited

U.S. PATENT DOCUMENTS

| | | | |
|---|---|---|---|
| 3,693,417 | 9/1972 | Fritz et al. | 73/81 |
| 3,956,924 | 5/1976 | Hansen et al. | 73/81 |
| 4,132,224 | 1/1979 | Randolf | 128/2 S |
| 4,159,640 | 7/1979 | Leveque et al. | 73/81 |
| 4,245,496 | 1/1981 | Napetschnig | 73/83 |
| 4,364,399 | 12/1982 | Dashefsky | 128/774 |
| 4,503,865 | 3/1985 | Shishido | 128/774 |
| 4,621,523 | 11/1986 | Shabel et al. | 73/81 |
| 4,888,490 | 12/1989 | Bass et al. | 250/561 |
| 4,896,339 | 1/1990 | Fukumoto | 377/19 |
| 5,067,346 | 11/1991 | Field | 73/81 |
| 5,146,779 | 9/1992 | Sugimoto et al. | 73/81 |
| 5,373,730 | 12/1994 | Kovacevic | 73/81 |
| 5,433,215 | 7/1995 | Athanasiou et al. | 128/774 |
| 5,494,045 | 2/1996 | Kiviranta et al. | 128/774 |
| 5,503,162 | 4/1996 | Athanasiou et al. | 128/774 |
| 5,701,913 | 12/1997 | McPherson et al. | 600/587 |
| 5,766,137 | 6/1998 | Omata | 600/587 |

FOREIGN PATENT DOCUMENTS

| | | |
|---|---|---|
| 1092038 | 11/1967 | United Kingdom. |
| WO 97/05825 | 2/1997 | WIPO. |

OTHER PUBLICATIONS

Armstrong, C.G. and Mow, V.C. "Variations in the intrinsic mechanical properties of human articular cartilage with age, degeneration, and water content." *J. Bone Jt. Surg.*, 64–A:88–94, 1982.

Athanasiou, K.A. et al., "Biochemical properties of hip cartilage in experimental animal models." *Clin. Orthop. Rel. Res.*, 316:254–266, 1995.

Blair, D.M. and Halperin, H.R., "Hand–Held, Dynamic Indentation System for Measuring Myocardial Transverse Stiffness," *Biomed. Instrumentation & Technology* 30:517–525, 1996.

Bora. F.W. and Miller, G. "Joint Physiology, cartilage metabolism, and the etiology of osteoarthritis." *Hand Clin.* 3: 325–336, 1987.

Convery, F.R., Akeson, W.H., and Keown, G.H., "The repair of large osteochondral defects." *Clin. Orthop. Rel. Res.*, 82:253–262, 1972.

Dashefsky, J.H., "Arthroscopic measurement of chrondromalacia of patella cartilage using a microminiature pressure transducer." *Arthroscopy,* 3:80–85, 1987.

Fisher, S.P., Fox, J.M., and Del Pizzo, "Accuracy of diagnosis from magnetic resonance imaging of the knee." *J. Bone Jt. Surg.*, 73:2–10, 1991.

Halbrecht, J.L. and Jackson, D.W., "Office arthroscopy: A diagnostic alternative." *Arthroscopy,* 8:320–326, 1992.

(List continued on next page.)

*Primary Examiner*—Max Hindenburg
*Attorney, Agent, or Firm*—Greenlee, Winner and Sullivan, P.C.

[57] ABSTRACT

A handheld materials testing device is provided for measuring compressive properties of a material, preferably articular cartilage in vivo. The device is computer-controlled and provides a readout indicative of the desired compressive property, which in the case of bodily tissue, may be indicative of the state of health of the tissue. The device does not require precise perpendicular alignment and is preferably capable of compensating for force applied by the user against the tissue.

19 Claims, 20 Drawing Sheets

OTHER PUBLICATIONS

Hale, J.E. et al., "Indentation assessment of biphasic mechanical property deficits in size–dependent osteochondral defect repair." *J. Biomechanics,* 26:1319–1325, 1993.

Jurvelin, J. et al., "Softening of canine articular cartilage after immobilization of the knee joint." *Clin. Orthop. Rel. Res.,* 207:246–252, 1986.

Kempson, G.E. et al., "Correlations between stiffness and the chemical constituents of cartilage on the hyman femoral head." *Biochem. Biophys.,* 215: 70–77, 1970.

Lai, W.M. et al., "A triphasic theory for swelling and deformation behaviors of articular cartilage." *J. Biomechanical Eng.,* 113:245–258, 1991.

Lipshitz, H. et al., "In vitro wear of articular cartilage." *J. Bone Jt. Surg.,* 57:527–534, 1975.

Lyyra, T. et al., "Indentation instrument for the measurement of cartilage stiffness under arthroscopic control." *Med. Eng. Phys.,* 17:395–399, 1995.

Mak, A.F. and Mow, V.C., "Biphasic indentation of articular cartilage–I. Theoretical analysis." *Biomechanics,* 20:703–714, 1987.

McDevitt, C.A. and Muir, H. "Biochemical changes in the cartilage of the knee in experimental and natural osteoarthritis in the dog." *J. Bone Jt. Surg.* [*Br*], 58–B:94–101, 1976.

Mow, V.C. et al., "Biphasic indentation of articular cartilage –II. A numerical algorithm and an experimental study." *J. Biomechanics,* 22:853–861, 1989.

Noyes, F.R. and Stabler, C.L., "A system for grading articular cartilage lesions at arthroscopy." *The Journal of Sports Medicine.,* 17:505–513, 1989.

Outerbridge, R.E., "The Etiology of Chondromalacia Patellae," *J. Bone Jt. Surg.,* 43B:752–757, 1961.

Räsänen, T. and Messner, K. "Regional variations of indentation stiffness and thickness of normal rabbit knee articular cartilage." *J. Biomed. Mater. Res.,* 31:519–524, 1996.

Schenck, R.C. et al., "A biomechanical analysis of articular cartilage of the human elbow and a potential relationship to osteochondritis dissecans." *Clin. Orthop. Rel. Res.,* 299:305–312, 1994.

Tkaczuk, H. "Human cartilage stiffness: In vivo studies." *Clin. Orthop. Rel. Res.,* 206:301–312, 1986.

S3: Motor Drive Signal
S38: Motor Control Signal
S19: Test Activation Signal
S25: Strain Measurement Signal
m:   Total number of steps
n:   Indentation steps 5,904,658

HAND-HELD MATERIALS TESTER

CROSS REFERENCE TO RELATED APPLICATION

This application claims priority to provisional application no. 60/024,527, filed Aug. 23, 1996, incorporated herein by reference to the extent not inconsistent herewith.

BACKGROUND OF THE INVENTION

Normal articular cartilage functions to absorb shock, to bear load and to provide articulating surfaces for diarthorodinal joints. Articular cartilage differs from other musculoskeletal tissues in that it does not have the ability to repair itself following traumatic or pathologic afflictions. Because adult articular cartilage is avascular and acellular, healing of this tissue is very difficult to achieve [Bora, F. W. and Miller, G. "Joint Physiology, cartilage metabolism, and the etiology of osteoarthritis." Hand Clin. 3: 325–336, 1987]. The composition of articular cartilage varies with anatomical location on the joint surface, with age and with depth from the surface [Lipshitz, H. et al., "In vitro wear of articular cartilage." J. Bone Jt. Surg., 57:527–534, 1975].

Once the disease or trauma affects the health of articular cartilage, an inevitable degenerative process can occur [Convery, F. R., Akeson, W. H., and Keown, G. H., "The repair of large osteochondral defects." Clin. Orthop. Rel. Res., 82:253–262, 1972]. During cartilage degeneration, the amount of interstitial water increases, the proteoglycan content decreases, and the aggregation of proteoglycans decreases [McDevitt, C. A. and Muir, H. "Biochemical changes in the cartilage of the knee in experimental and natural osteoarthritis in the dog." J. Bone Jt. Surg. [Br], 58-B:94–101, 1976]. When the proteoglycan content decreases, cartilage becomes softer [Kempson, G. E. et al., "Correlations between stiffness and the chemical constituents of cartilage on the human femoral head." Biochem. Biophys., 215: 70–77, 1970; Jurvelin, J. et al., "Softening of canine articular cartilage after immobilization of the knee joint." Clin. Orthop. Rel. Res., 207:246–252, 1986].

The condition of cartilage can be evaluated using various methods including visual examination, mechanical probing, imaging diagnostics, and biopsies. Clinically it is very difficult to evaluate cartilage health in a non-destructive manner and most often visual observations made arthroscopically in conjunction with mechanical probing are used. Visual examination is basically a subjective, qualitative determination of the structural integrity of the surface and includes a description of the articular cartilage damage present. Numerous systems have been proposed over the years, including the Outerbridge and Noyes classification systems [Noyes, F. R. and Stabler, C. L., "A system for grading articular cartilage lesions at arthroscopy." The Journal of Sports Medicine., 17:505–513, 1989; Outerbridge, R. E., J. Bone Jt. Surg. 43B:752–757, 1961]. Mechanical probing utilizes a hand-held probe like a nerve hook to subjectively evaluate the stiffness of the articular cartilage. This instrument has traditionally been easy to use in an arthroscopic setting, but the information obtained is not traceable over time. Imaging diagnostics, specifically Magnetic Resonance Imaging (MRI), can be used to diagnose internal derangements of joints. Even though its overall accuracy range is acceptable [Fisher, S. P., Fox, J. M., and Del Pizzo, "Accuracy of diagnosis from magnetic resonance imaging of the knee." J. Bone Jt. Surg., 73:2–10, 1991], its cost, lack of sensitivity for lesions of the articular cartilage [Halbrecht, J. L. and Jackson, D. W., "Office arthroscopy: A diagnostic alternative." Arthroscopy, 8:320–326, 1992], and unsuitability for some patients makes it undesirable in many cases.

Many researchers have confirmed the correlation of the cartilage stiffness with the condition of the cartilage [Kempson, G. E. et al., "Correlations between stiffness and the chemical constituents of cartilage on the human femoral head." Biochem. Biophys., 215: 70–77, 1970], and it has been shown that the compressive stiffness of the cartilage is primarily determined by proteoglycans [Armstrong, C. G. and Mow, V. C. "Variations in the intrinsic mechanical properties of human articular cartilage with age, degeneration, and water content." J. Bone Jt. Surg., 64-A:88–94, 1982]. Kempson, supra, reported that the greater the proteoglycan content, the stiffer the cartilage. Indentation of cartilage has been used extensively in vitro [Athanasiou, K. A. et al., "Biochemical properties of hip cartilage in experimental animal models." Clin. Orthop. Rel. Res., 316:254–266, 1995; Schenck, R. C. et al., "A biomechanical analysis of articular cartilage of the human elbow and a potential relationship to osteochondritis dissecans." Clin. Orthop. Rel. Res., 299:305–312, 1994; Hale, J. E. et al., "Indentation assessment of biphasic mechanical property deficits in size-dependent osteochondral defect repair." J. Biomechanics, 26:1319–1325, 1993; Mak, A. F. and Mow, V. C., "Biphasic indentation of articular cartilage—I. Theoretical analysis." Biomechanics, 20:703–714, 1987; Räsänen, T. and Messner, K. "Regional variations of indentation stiffness and thickness of normal rabbit knee articular cartilage." J. Biomed. Mater. Res., 31:519–524, 1996] and in situ [Lyyra, T. et al., "Indentation instrument for the measurement of cartilage stiffness under arthroscopic control." Med. Eng. Phys., 17:395–399, 1995; Tkaczuk, H. "Human cartilage stiffness: In vivo studies." Clin. Orthop. Rel. Res., 206:301–312, 1986; Dashefsky, J. H., "Arthroscopic measurement of chondromalacia of patella cartilage using a microminiature pressure transducer." Arthroscopy, 3:80–85, 1987] to measure the material properties of articular cartilage including stiffness. To biomechanically evaluate the articular cartilage, in vitro biphasic and even triphasic creep indentation and stress relaxation tests have been used to determine the intrinsic mechanical properties (aggregate modulus, Poisson's ratio, permeability) of the articular cartilage [Mow, V. C. et al., "Biphasic indentation of articular cartilage—II. A numerical algorithm and an experimental study." J. Biomechanics, 22:853–861, 1989; Lai, W. M. et al., "A triphasic theory for the swelling and deformation behaviors of articular cartilage." J. Biomechanical Eng., 113:245–258, 1991]. In addition in situ indentation tests have been used to map various regions of articular cartilage in several animal models and show significant variations in stiffness among the various test sites [Räsänen, T. and Messner, K. "Regional variations of indentation stiffness and thickness of normal rabbit knee articular cartilage." J. Biomed Mater Res., 31:519–524, 1996].

In the literature a few devices for the measurement of cartilage stiffness in a clinical setting have been reported [e.g. Lyyra, T. et al., "Indentation instrument for the measurement of cartilage stiffness under arthroscopic control." Med. Eng. Phys., 17:395–399, 1995; Tkaczuk, H. "Human cartilage stiffness: In vivo studies." Clin. Orthop. Rel. Res., 206:301–312, 1986; Dashefsky, J. H., "Arthroscopic measurement of chondromalacia of patella cartilage using a microminiature pressure transducer." Arthroscopy, 3:80–85, 1987]. Lyyra et al. use an indentation instrument for the measurement of cartilage stiffness under arthroscopic control. Based on tests in laboratory conditions with elastomer and cadaver knee joint cartilage samples, the authors concluded that such an instrument was suitable for qualitative detection of cartilage stiffness.

The desire to test compressive mechanical properties of a material existed long before a correlation between articular cartilage stiffness and the existence of articular degenerative diseases was recognized. Many devices are known for use in material indenting which are unsuitable for use for measuring cartilage stiffness due to their design. Some of the devices such as those of U.S. Pat. No. 5,146,779 (Sugimoto), U.S. Pat. No. 4,896,339 (Fukumoto), and U.S. Pat. No. 5,067,346 (Field) are designed for use on a tabletop. Since they cannot be used arthroscopically, a sample of tissue would have to be removed from the body or the patient would have to be subjected to major invasive surgery in order to allow these devices to indent the articular cartilage. Due to the injury to the patient and the expense these procedures would necessarily entail, a nonarthroscopic design is not effective for testing the in vitro stiffness of articular cartilage.

U.S. Pat. No. 5,433,215 (Athanasiou et al.) and Tkaczuk, H. "Human cartilage stiffness: In vivo studies." *Clin. Orthop. Rel. Res.,* 206:301–312, 1986 disclose devices useful for cartilage testing; however, these devices are larger and more awkward to use than would be desirable. These devices cannot be used arthroscopically and require the joint surfaces to be tested to be completely exposed.

In order to prevent the invasive steps and awkwardness involved in the use of the above designs to measure articular cartilage, hand-held materials testers have been designed which require no more surgery than a visual arthroscopic evaluation. These, however, suffer from a plethora of other problems. U.S. Pat. No. 4,159,640 (Leveque) describes a hand-held device which is not usable for arthroscopic surgery. Leveque's device requires a necessarily wide base suited for surface tissue measurements such as skin or the surface of muscle, but is unsuited for use within joints for measurement of articular cartilage. In addition, Leveque's device must be positioned relatively perpendicular to the material to be tested and the entire device must rest on material of similar stiffness in order to accurately measure.

U.S. Pat. No. 4,503,865 (Shishido) is primarily designed to measure differences between compressibilities. The device rolls over the material and allows measurement of changes of stiffness. The device however has no means for measuring absolute stiffness and providing an objective display of stiffness. The force the operator uses to position the device will affect the results, and this force exerted by the operator is not controlled. The device can thus be used to find hard or soft spots within a specific material, but the device cannot provide a concrete determination of whether the material is soft or hard as compared to an objective standard.

The major limitation with arthroscopic devices intended to be used for measurement of mechanical properties of materials is that they do not compensate for the indenting tip being positioned at angles other than perpendicular with the material being tested. This can either be due to natural variation in the surface of the material or to difficulty on the part of the operator to maneuver the tip to a position where the tip is perpendicular. Some devices have tried to compensate for this by forcing the material to be placed perpendicular to the indenting tip (the table-top models listed above), while others have tried to ensure that the operator can effectively know when the tip is perpendicular to the material. U.S. Pat. No. 4,364,399 (Dashefsky) discloses a probe whose compressible tip is pressed into the cartilage. Due to the shape of the end of the cannula, when the operator can push no further, the compressible portion of the probe registers the appropriate stiffness (see FIG. 3B of Dashefsky for the position for a proper reading). The probe is positioned manually and perpendicularity of the probe is subjectively determined. There is no guarantee that the operator has correctly aligned the probe for any given measurement. The manual identification process is not sufficiently accurate to allow repeatable, objective measurements. U.S. Pat. No. 4,132,224 (Randolf) also discloses a device which is positioned manually and provides no means for compensation for movement. It is clear from the description of its operation that any tilting leading to the tip not being perpendicular will result in significantly inaccurate readings due to premature touching of the forked beam of this device. U.S. Pat. No. 5,503,162 (Athanasiou et al.), U.S. Pat. No. 5,494,045 (Kiviranta et al.), and Lyyra, T. et al., "Indentation instrument for the measurement of cartilage stiffness under arthroscopic control." *Med. Eng. Phys.,* 17:395–399, 1995 describe devices having a contact surface around the tip to aid in aligning the tip perpendicular to the material being tested (in addition to using machine controls to aid alignment in Athanasiou et al.), but such additions, although aiding the operator in positioning the tip perpendicular to the test material, do not help if the operator cannot get the tip perpendicular. In all of these devices, and others, the indenting tip must be perpendicular in order for an accurate measurement of stiffness to be made. No matter how many structures are added to these devices to try and insure perpendicularity, they will all give significantly inaccurate readings if the indenting tip cannot be aligned perpendicular to the material to be tested. In articular cartilage measurements, especially in small joints such as finger, ankle, or temporal mandibular joints, there is a high possibility that the device cannot be aligned perpendicular to the material being tested due to intervening structures such as bone, muscle, or other body parts. There is thus a need in the art for a materials tester that does not have to place its indenting tip perpendicular to the material being tested in order to provide accurate measurements.

In addition to these limitations, devices known to the art are usually unable to compensate for temperature variations during the measurement. The art makes limited reference to compensating for temperature effects although such effects can significantly impact the measurements of the device, especially when measurements are taken in situ in the body with devices calibrated outside the body.

These devices often also indent the material great distances over long periods of time. Although for many materials such indentation time and distance are not relevant, in the case of articular cartilage, long, deep indentation steps can result in significant tissue damage.

Furthermore, the operator may introduce error due to the varying amounts of force the operator uses to bring many prior art devices into contact with the material to be tested. In a table top device this is not a problem since the operator need not hold the device against the material, but may place the material on a prepared surface and allow indentation controlled by machine or computer. In many hand-held devices known to the art, however, if the operator changes the force used to depress the testing tip of the device into the material to be tested, the device will report compressibilities of different values.

Finally, none of these devices are designed to allow the portion inserted into the patient's body to be for single use only. Since a device for single use is significantly more sterile and sanitary than a reused device, such a quality is to be desired. Known devices are generally not completely watertight and thus submersible which affects their ability to be sterilized via liquid sterilization methods and also makes them vulnerable to splashes, from body fluids or otherwise, that could damage their delicate electronic components. For a device used in situ for the measurement of body tissue stiffness, survivability under surgical conditions where fluids are prevalent is a highly desired quality.

It is an object of the invention to provide a novel materials testing device which is free of the above-mentioned defects of the art.

SUMMARY OF THE INVENTION

The present invention provides a materials testing device for measuring the compressive properties of a material by indenting the material surface and measuring the resistance of the material to the indention. Compressive properties include but are not limited to: stiffness, Young's modulus, and hardness.

The following discussion is primarily directed to measuring stiffness; however, Young's modulus and hardness may also be measured by the device. "Stiffness" in the context of this application is generally taken to mean the resistance of a material to a force exerted upon it.

The device of this invention allows measurements in positions where the tip physically cannot be aligned perpendicular to the material being tested, simplifies the operation by allowing the operator more freedom in aligning the device, and improves accuracy by being resistant to error from the positioning of the device.

"Perpendicular" alignment in this instance refers to the angle made between the axis of motion of the indenting tip and the flat surface of the material to be tested at the point of contact. The indenting tip need not be perpendicular to any structures on the device.

The device of the present invention measures compressive properties (stiffness) of a material and comprises: an indenting tip, a loading system moving a certain linear distance and pushing said indenting tip into the material to be tested, a force detection system for measuring force exerted on said indenting tip by the material being tested, a variable angle compensation system for compensating for the effects of tilt of the indenting tip away from perpendicular alignment on the force detected by said force detection system, and a rendering system for converting output of said force detection system to a display representative of the desired compressive properties.

The device may further comprise a temperature compensation system for allowing the device to measure accurately even when calibrated at a temperature significantly different from the temperature at which the device is measuring. The device may also incorporate an applied force compensation system to compensate for the effects of the user applying force on the device into the material to be tested. The device is preferably constructed of two separable parts where the part entering the body of a patient is designed for single use only to increase sterility. The device, and specifically the non-disposable portion of the device, may also be watertight so that its delicate electronic components are not damaged by fluids and the device can be subjected to sterilization methods involving the use of fluids.

The device is usable for measuring the properties of multiple different types of materials including, but not limited to, body tissues known to the art, e.g., cartilage, skin, or organ fibers including soft tissues known to the art, e.g., muscle or connective tissue, or man-made synthetic materials known to the art, e.g., plastics, rubber, or foam. These materials can be measured in vitro, in situ, in vivo, or under any other working conditions where measurement of compressive properties is desired.

The indenting tip is a piece of rigid material capable of indenting the material to be tested and capable of having force exerted upon it without deforming.

The loading system comprises any system known to the art for moving a certain linear distance and pushing the indenting tip into the material to be tested. The distance moved by the loading system must be "certain" in that it has to either be set in advance, or the loading system must contain structures allowing accurate measurement of the distance the loading system has moved. In a preferred embodiment, the loading system comprises a computer-controlled linear actuator (stepper motor) and a drive shaft assembly moved by said motor which may comprise multiple components for translating the movement of the actuator in one direction to movement of the testing tip in another direction. The number of steps taken by the motor is also recorded via a computer-controlled feedback system in one embodiment.

The force detection system may be any system known to the art for measuring the force that is exerted on the indenting tip by the material being tested. In the preferred embodiment the system comprises a combination of one or more semi-conductor strain gauges attached to a sensing arm which holds the indenting tip. The force detection system may also comprise an electrical circuit attached to the strain gauges that can interpret the output of the strain gauges as uncompensated (raw) force on the indenting tip.

The variable angle compensation system comprises any means known to the art for compensating for the effects of tilt of the indenting tip on the force measurement. This may be either a passive system comprising means for ensuring that tilt has little or no effect on the force exerted by the indenting tip against the material being tested, e.g., a properly shaped indenting surface on the indenting tip, or may be an active system that allows for the calculation of the force on the indenting tip by the material, compensating for tilt. Both pitch, the tilt caused by the handpiece of the device being raised and lowered, and roll, the motion caused by the handpiece being circularly rotated side to side, must be compensated for and are considered "tilt" in this device. In a preferred embodiment, this system comprises or consists essentially of a rounded surface of the indenting tip, most preferably of paraboloid shape. This system passively compensates for tilt of the indenting tip. Other systems for correcting tilt may also be used. The system can incorporate other apparatuses such as those described in U.S. Pat. No. 4,888,490 (Bass et al.) incorporated herein by reference, lasers, or other light sources or external markings to be used to determine the exact offset of the testing tip from perpendicular alignment based on physical principles. Any of these systems may incorporate computer-controlled feedback mechanisms or other systems known to the art to calculate and mathematically compensate for the angle of the tip. The system may also incorporate an angle error system that warns the user if the error due to the angle of the tip with respect to the surface of the material being tested goes outside a specified range for accuracy in the desired stiffness readings.

A "rendering system" as used herein is a system comprising means for converting the stiffness measurement received or computed by a processor into a useful representation of a desired compressive property and displaying said useful representation, e.g., by printing, electronic digital display, audio means, or otherwise, which renders a desired representation of the measured property, such as a numerical, graphical, symbolic, or other representation.

The temperature compensation system is a system that is either passively resistant to changes in temperature or actively compensates for errors caused by the temperature at which the measurements are taken. In a preferred embodiment, the temperature compensation system comprises strain gauges and associated circuitry used in the force detection system which compensate for and/or are resistant to changes in temperature. The temperature compensation system may also comprise compensation means such as a temperature detector known to the art combined with a computerized compensation calculation known to the art. The system is preferably able to compensate for temperature independent of the medium in which the device is submerged, including media such as water, body fluids, or air.

The device may also comprise an applied force compensation system comprising any means known to the art of mechanical or electrical design which passively or actively compensates for force applied by the user. In the preferred embodiment this comprises mechanical design elements such as chamfering of the indentation hole or similar outer shaft contouring. In addition mechanical support to prevent the drive shaft from flexing, such as reinforcements to the drive shaft or alternative structures to prevent flexing, is used. Alternatively the applied force compensation system could be a second strain gauge system dedicated to the measurement of user-applied force. The system may also incorporate an internal computer-controlled feedback mechanism which measures the user's applied force and adjusts the value of the measured output or limits the range at which testing may occur. Other systems known to the art to ensure that the measured value remains within acceptable accuracy may also be utilized.

Preferably the device consists of two primary parts with the piece designed for use within the body (probe) being disposable after single use. In order to insure that the probe is only used once, it preferably contains structures which cause it to cease functioning after single use or any attempt to sterilize it. Some means for doing this include heat sensors or fuses which allow the device to turn on only once, a "safety pin" design that springs open and breaks after use, or a circuit with a filler that melts during the first use resulting in a destroyed electrical connection.

In order for the device to be watertight, all connections need to be properly sealed. This is generally accomplished through the use of sealants such as, but not limited to, epoxies or silicones as known to the art for permanent connections or screw and O-ring combinations for connections which are desired to be opened for storage, two-part construction, or repair. "Watertight" means that all delicate electrical components, or any other components that would be affected by being submerged, are protected by a casing having substantial impermeability not only to water, but also to other common liquids present in medical applications including sterilizing solutions and body fluids. For safety, a watertight device of the present invention is not assumed to be watertight when attached to its power system but is disconnected prior to immersion of parts containing electronic components. The present invention can also be adapted to be watertight when attached to its power system under any forseen usage.

DETAILED DESCRIPTION

Figure 1:
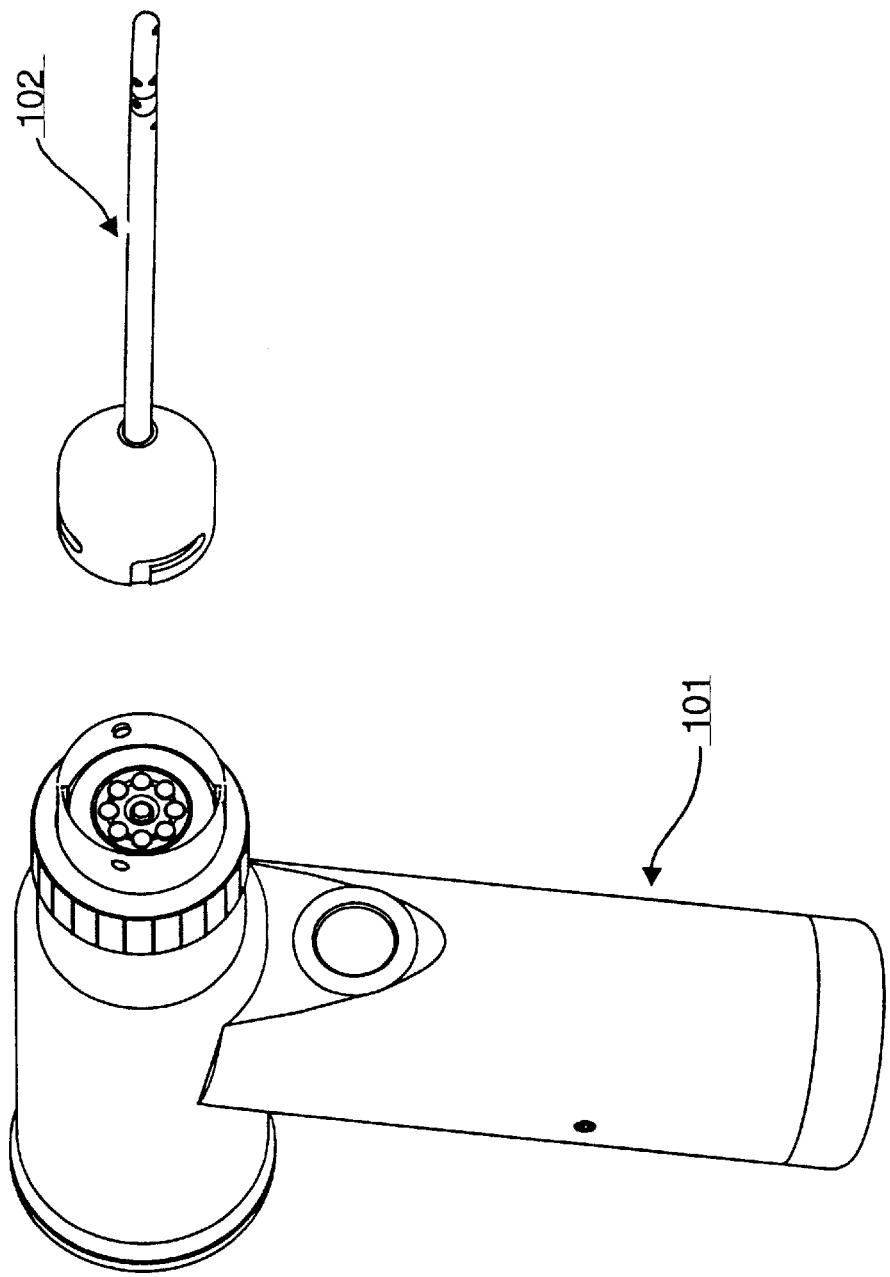
FIG. 1 shows a three-dimensional front view of the device.
Figure 2:
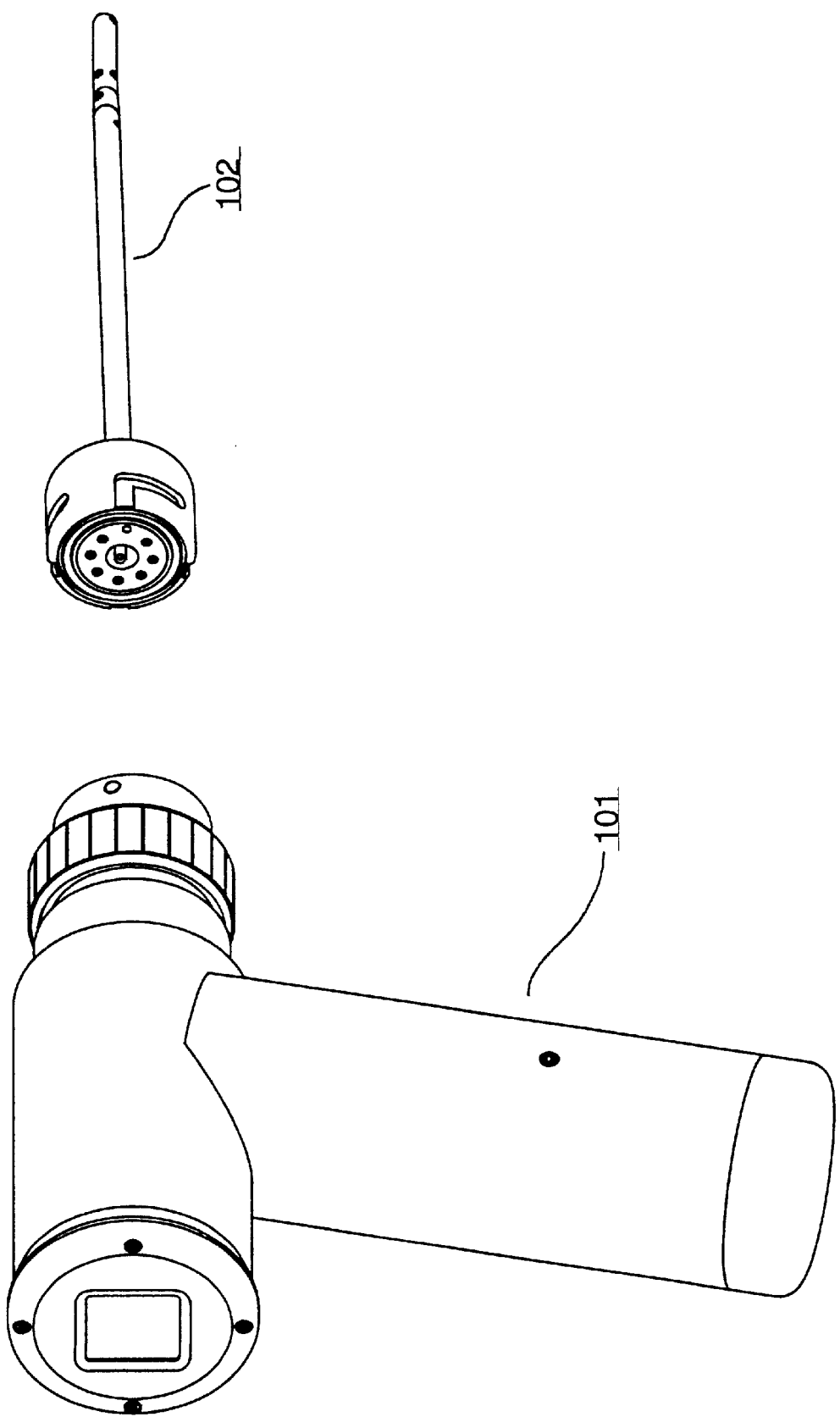
FIG. 2 shows a three-dimensional rear view of the device.

The device consists of two main components shown in FIG. 1 and FIG. 2: the handpiece 101 and the probe 102. In the preferred embodiment the probe 102 is made for single use and inexpensive enough to make such single use worthwhile, and the handpiece 101 is designed to be reused. The probe preferably contains mechanical means to make it inoperative if an additional sterilization attempt were made, e.g. heat sensors or fuses which allow the device to turn on only once, a safety pin design that springs open and breaks after a single use, or a circuit with a filler that melts during the first use so the device will no longer function. Preferably, the probe 102 can also be of varying diameters from about 2 mm for very small joints such as fingers, ankles or temporal mandibular joints to larger diameters, such as about 5 mm for other joints, thus allowing the operator to select a probe most suitable for the given task.

Figure 3:
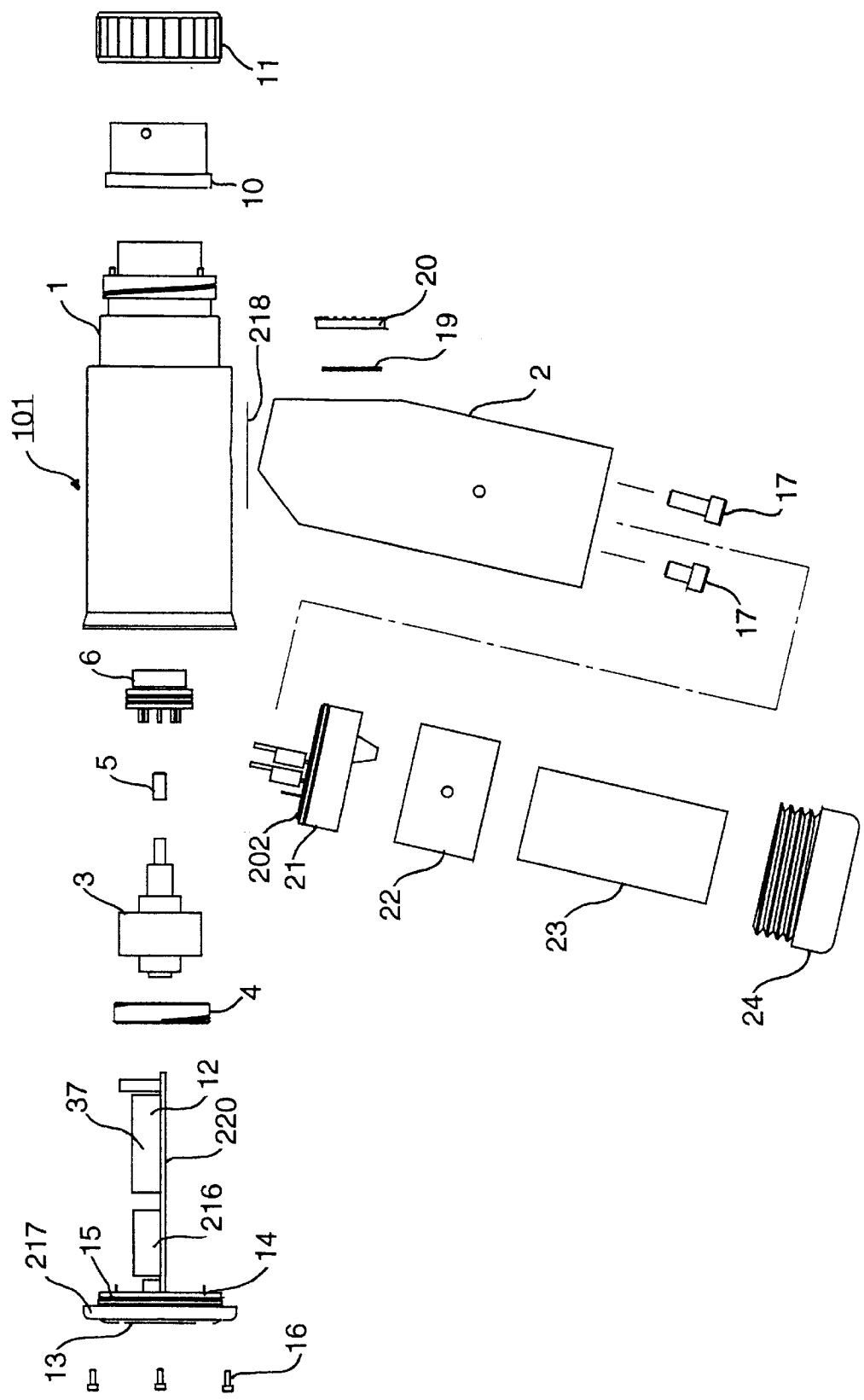
FIG. 3 depicts an exploded view of the main components of the handpiece.
Figure 4:
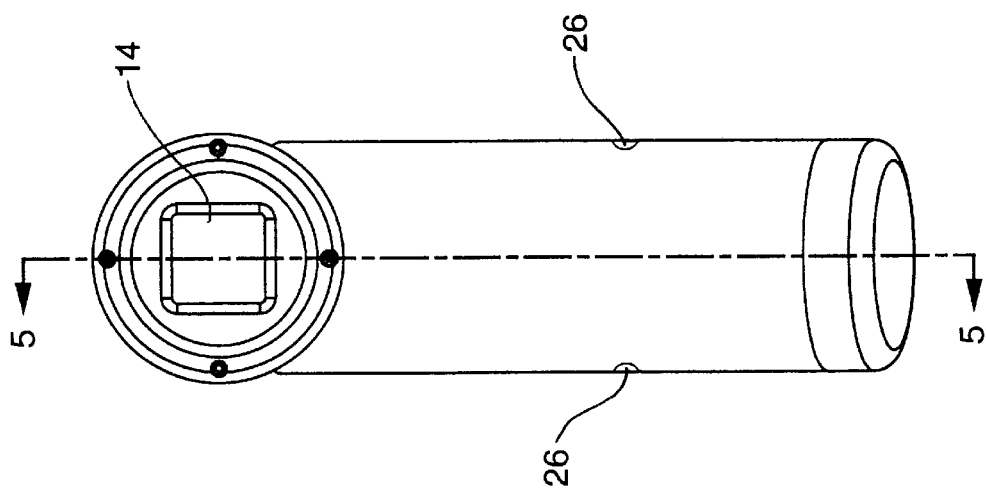
FIG. 4 depicts a rear view of the handpiece.
Figure 5:
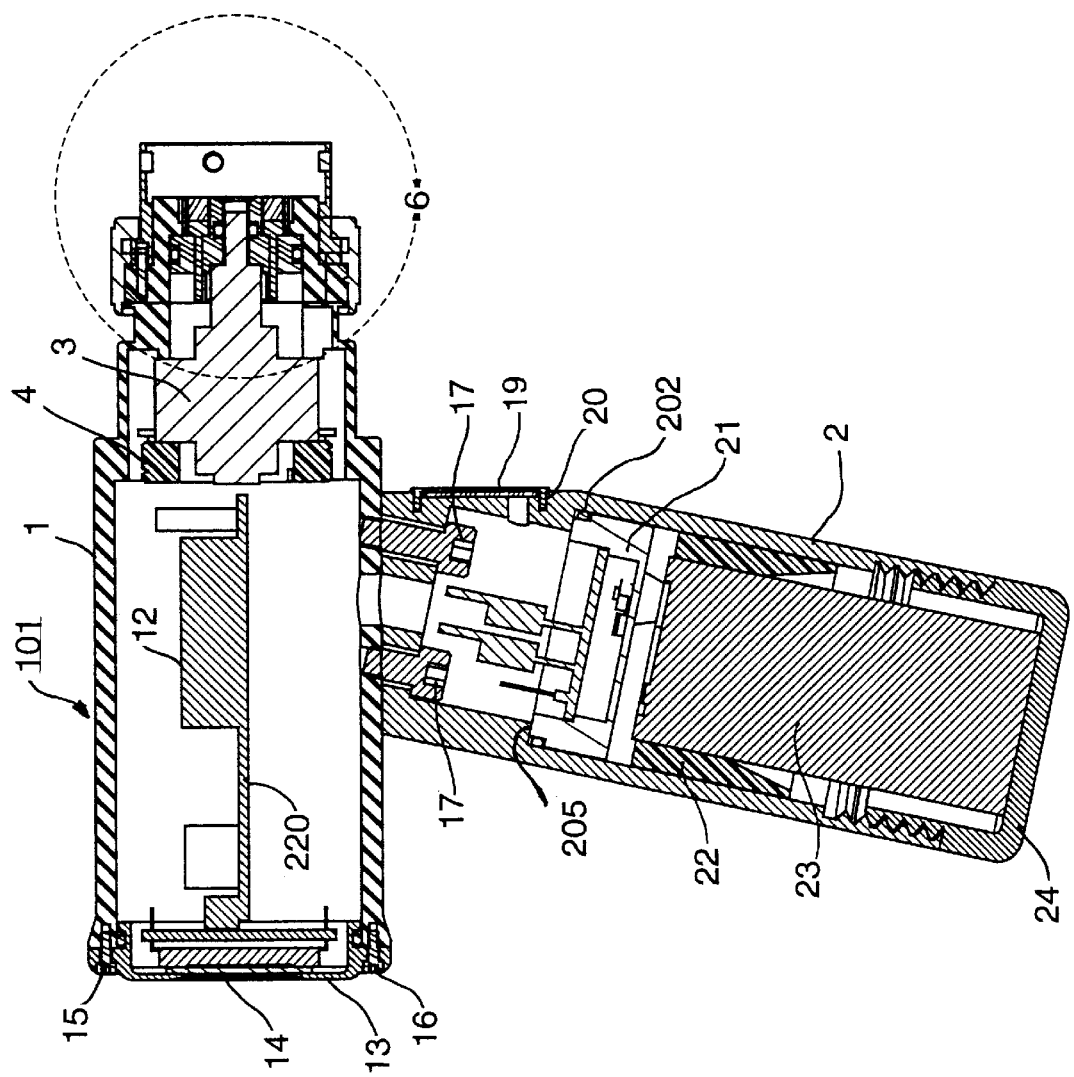
FIG. 5 depicts a longitudinal cross-section of the handpiece along line 5—5 of FIG. 4 with all of its components in place. Wiring is not shown

FIGS. 3 and 5 show the primary components of the handpiece 101. FIG. 3 shows the major components of the handpiece exploded. FIG. 4 is a rear view of the handpiece showing display 14 and alignment screws 26 while FIG. 5 is a cross-section of the handpiece along line 5—5 of FIG. 4 and shows the components in place as they would be when the device is assembled.

Referring to FIG. 3, the handpiece 101 primarily consists of the housing 1, and the handle 2. At the forward end of the housing 1 is the coupler ring 10 for engaging the probe 102 (FIG. 1). A tightener 11 screws down over coupler ring 10 when the probe 102 is in place to firmly secure the probe to the handpiece 101. When the components are connected correctly, the handpiece contact holder 6 at the front end of housing 1 will be in electrical connection with the probe which is now inside handpiece 101, and the connection will be watertight. The housing 1 further contains a motor 3, which in the preferred embodiment is a linear actuator (stepper motor), but could be any kind of motor so long as systems are present to determine its movement a certain linear distance. At the moveable end of the motor 3 an interface button 5 is attached. The interface button 5 allows the motor's movement to be translated to components within the probe. The motor is held in position by a motor retainer 4 which preferably is a plastic ring able to screw tightly behind the motor 3 but could be any means for maintaining the position of the motor 3. The housing 1 also further contains the main electronics module 12 which preferably is a printed circuit board containing the necessary components for the processor 37 as well as the electronic components of the rendering system, the motor drive circuit, and for amplification of the raw force signal. The main electronics module 12 need not contain all of these structures and may contain alternative electronic structures or a combination of these structures and alternative structures. The main electronics module 12 is preferably attached to the housing by a removable chassis 220 which in the embodiment shown is the same as the circuit board of module 12. The rendering system for converting a signal preferably has multiple components including a display 14, visible through back window 13, and speaker 216 connected to the main electronics module 12. In a preferred embodiment, the display 14 is a liquid crystal display (LCD) designed to provide the user with the measurement data as well as error feedback, low battery, and battery exhausted displays. The LCD screen is positioned so that it is visible through a back window 13 contained within a rear panel 217. Alternatively the display 14 could consist of a graphic LCD, a collection of LEDs, an external monitor or video overlay connected to the handpiece 101 by way of cable, IF or RF, or any other display or combination of displays as known in the art. In a preferred embodiment Speaker 216 will further emit audio signals, e.g., tones, digitized speech, or any other form of audio to supplement the visual message on display 14. The rear panel 217 is attached to the housing 1 by means of a watertight seal. In a preferred embodiment this seal is created through the use of a rear O-ring 15 and rear screws 16, most preferably four in number.

The handle 2 is attached to the housing 1 by any means known to the art, preferably using handle screws 17 and a sealant means such as liquid sealant, an O-ring, or adhesive at the handle junction 218; most preferably the handle 2 is attached by two handle screws 17 of different length and with liquid sealant. The handle junction 218 allows electrical contact between the handle electronics module 21 and the components within the housing 1. At the upper front of the handle 2 is a switch 19, preferably a momentary action switch. Within handle 2 is handle electronics module 21, seated atop and engaged with aligner 22, and electronically connected to power system 23 within aligner 22. These components are held in place by handle base 24 attached using screw threads or otherwise attachable to handle 2.

Referring to FIG. 5, the switch 19 is secured at the top of the handle 2 with a bezel 20. Preferably, an adhesive is used to hold the bezel 20 in place and provide for a seal.

The handle electronics module 21 rests against a lip 205 on the inside diameter of the handle 2 and is held in place by any means known to the art, preferably an adhesive, most preferably an epoxy. A handle electronics module O-ring 202 around the handle electronics module 21 provides a watertight seal. The handle electronics module 21 preferably contains electrical components for regulating the power supplied by the power system 23 to all electrical components of the device. In a preferred embodiment the power system 23 is a battery pack consisting of multiple nickel-cadmium (NiCd) batteries of about 9.6 total voltage connected in series, the battery pack being rechargeable on an external recharging system (not shown) like those known to the art. Most preferably 8 size $2/3$ AA batteries rated at 270 mAh are used. Alternatively, disposable (nonrechargeable) batteries could be used. The power system may also consist of an external cable system allowing the use of external AC or DC power sources (not shown). The power system 23 is secured by the aligner 22 and handle base 24 when in use. In the most preferred embodiment, the handle base 24 contains screw threads allowing the handle base 24 to be screwed into the bottom of the handle 2. Alternatively the handle base 24 may utilize a snap-in mechanism consisting of latching features on the battery pack which engage inside the handle and allow for quick release when the latches are depressed. Additionally the handle base 24 can be secured by other permanent or removable attachment mechanisms as recognized in the art. The aligner 22 is any material known to the art allowing electronic leads on the power system 23 to be placed securely in contact with electronic leads on the handle electronics module 21 preferably through the use of a contact spring. The power system 23 is then secured by the above mentioned handle base 24. The aligner 22 is fastened inside the handle by any means known to the art, preferably alignment screws 26 (not shown in this view; see FIG. 4), most preferably numbering two.

Figure 6:
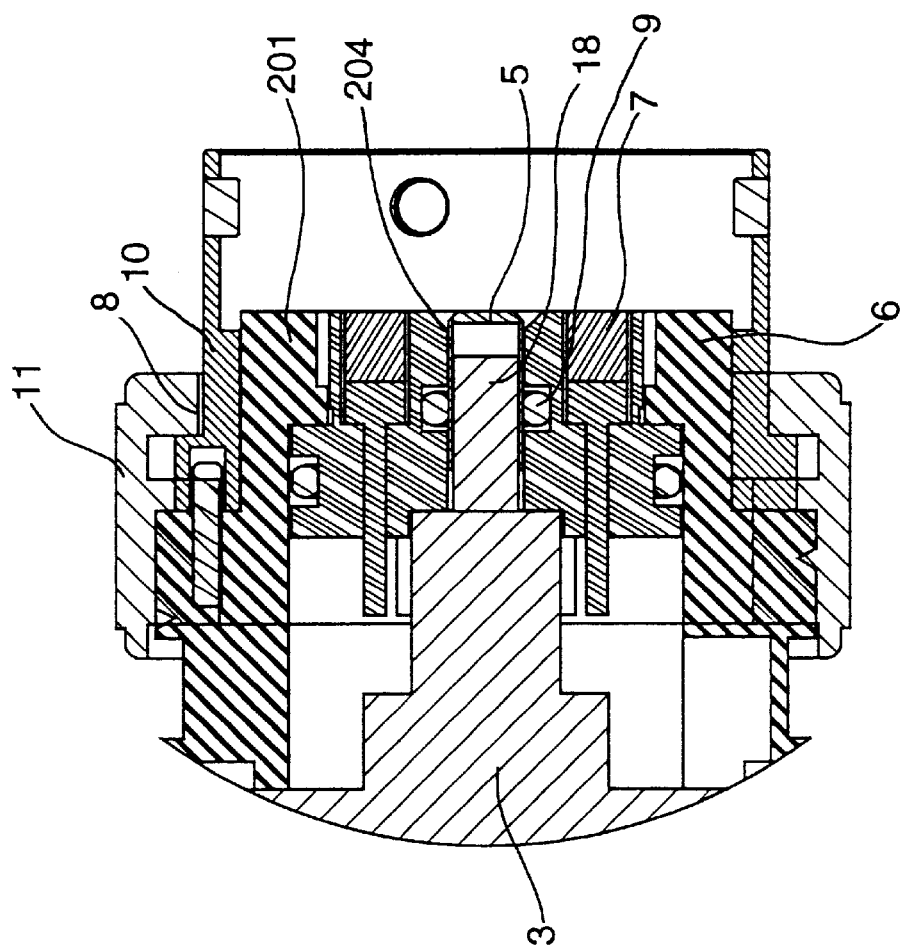
FIG. 6 depicts an enlarged view of the section of FIG. 5 indicated by dotted circle 6 showing the structures on the front end of the device.

FIG. 6 provides further details from within the dotted line -6- of FIG. 5 of the front of the handpiece and the handpiece contact holder 6. The handpiece contact holder 6 comprises handpiece electrical contacts 7 which in a preferred embodiment may consist of a bellow spring welded onto a pin and sit flush with the housing face 201. Contact holder O-ring 8 located in an external groove of the housing contact holder 6 provides a tight fit with the housing 1 holding the housing contact holder 6 in place and providing a watertight seal. The motor 3 with the interface button 5 attached sits in the front part of the housing with the motor shaft 18 extending through a central hole 204 in the housing contact holder 6. Motor O-ring 9 is located in an internal groove of housing contact holder 6 and provides a watertight seal between interface button 5 and housing contact holder 6.

Figure 7:
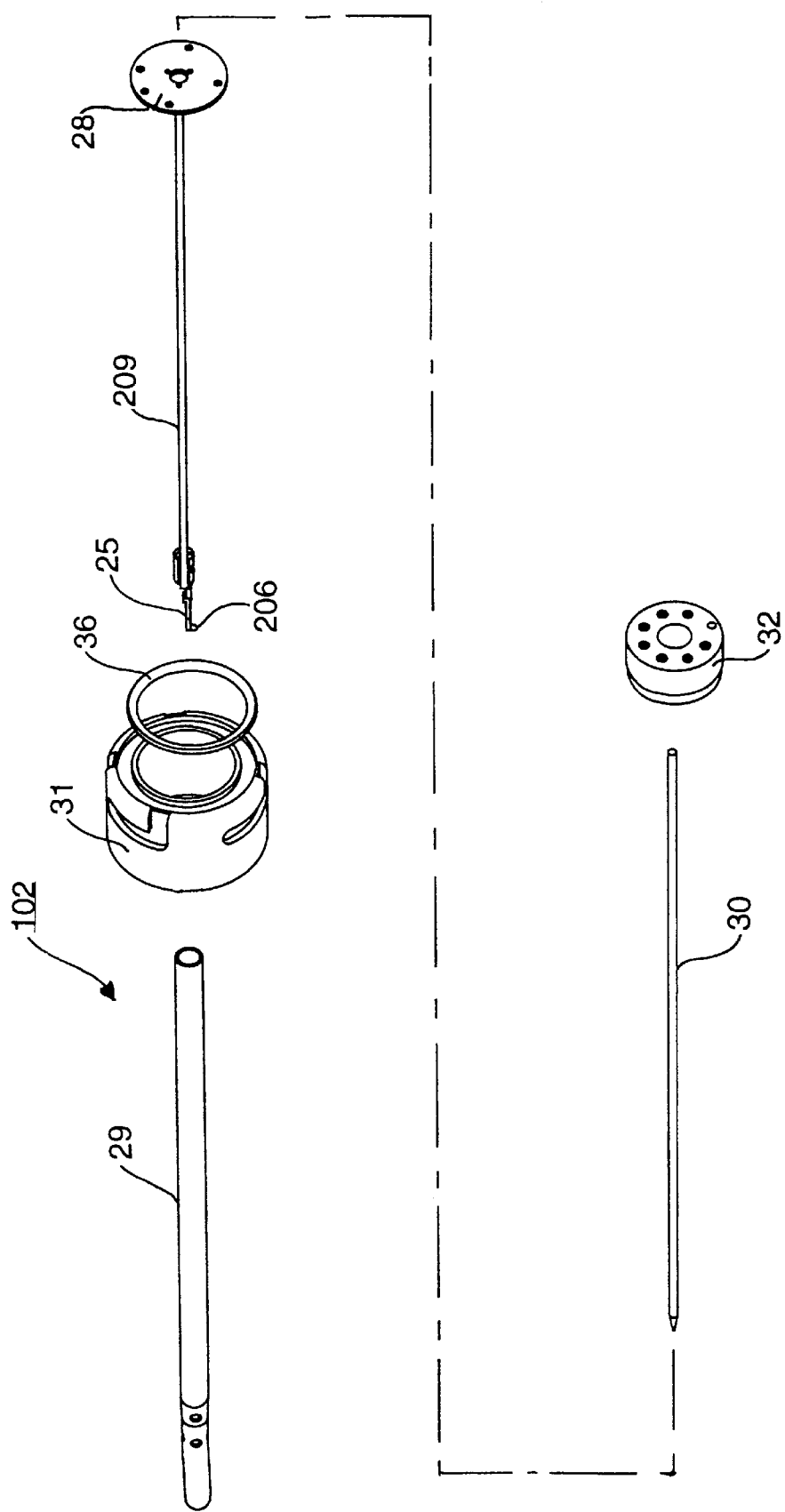
FIG. 7 shows an exploded view of the main components of the probe.

The main components of probe 102 are shown in FIG. 7. The probe 102 primarily consists of a sensing arm 25, the indenting tip 206, outer shaft 29, drive shaft 30, connecting base 31, probe electronics module 28, probe O-ring 36 and probe contact holder 32.

Figure 8A:
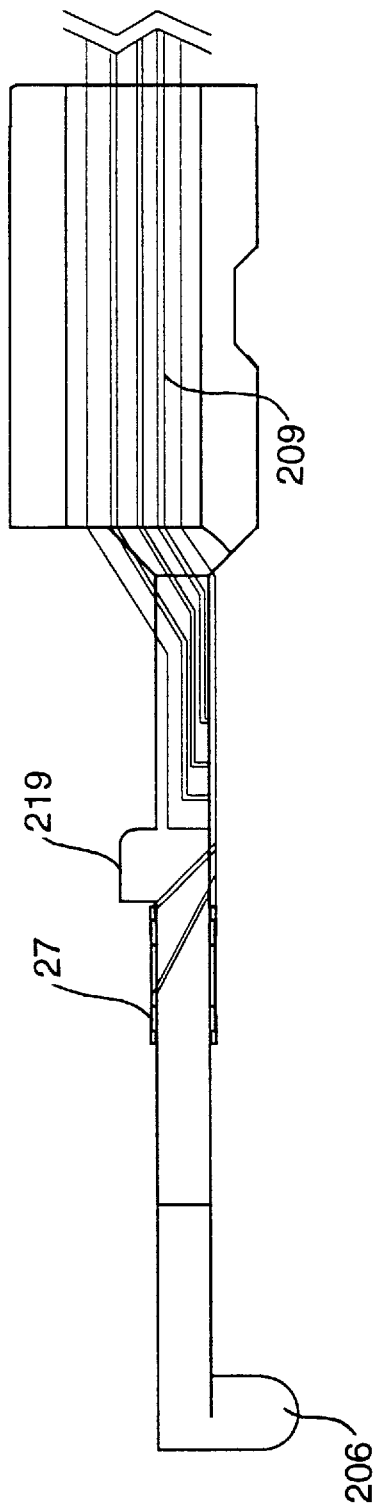
FIG. 8 shows details of the sensing arm and force-detection system. 8A is a side view, 8B is a bottom view.
Figure 8B:
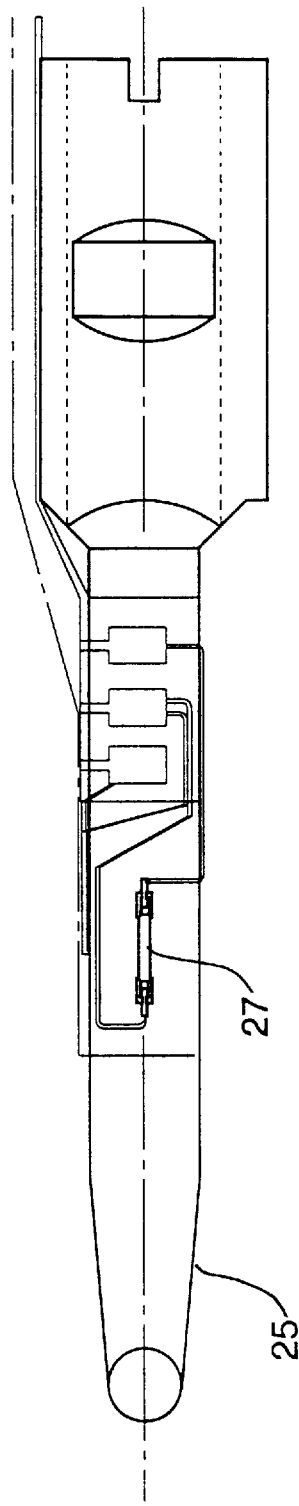

FIG. 8A is a side view and FIG. 8B is a bottom view of the device showing details of a preferred embodiment of the force detection system. The sensing arm 25 has a bend shown as 90° in FIG. 8A near the end which terminates in the indenting tip 206 and a ridge 219 capable of contacting drive shaft 30 (not shown, see FIG. 11). The bend can be any angle allowing the indenting tip 206 to extend through a corresponding indenting hole 207 (FIG. 11) near the front of the outer shaft 29 (FIG. 11) to allow for additional flexibility in positioning of the device during measurement. In order to accomplish angles other than 90°, additional components of the drive shaft, or a different shape of sensing arm may be required (not shown). The strain gauges 27 measure the bend in the sensing arm 25 producing a raw force signal S215 (FIG. 17) by any means known to the art which allows a computation of the force applied on the indenting tip 206, preferably using the different force values from each strain gauge. The strain gauges 27 are preferably semiconductor strain gauges but could alternatively be thin film strain gauges or other strain gauges as is known to the art. The strain gauges are electrically connected to appropriate structures on the probe electronics module 28 (FIG. 11) through wiring 209 which is preferably a ribbon cable but alternatively could be insulated wires or any other means of transferring electrical signals as is known to the art. In the preferred embodiment the strain gauges 27 and the probe electrical contacts 33 (FIG. 11) are watertight. This can be achieved by any means known to the art but is preferably accomplished by covering the strain gauges 27 and the probe electrical contacts 33 (FIG. 11) with an impermeable coating.

Figure 9A:
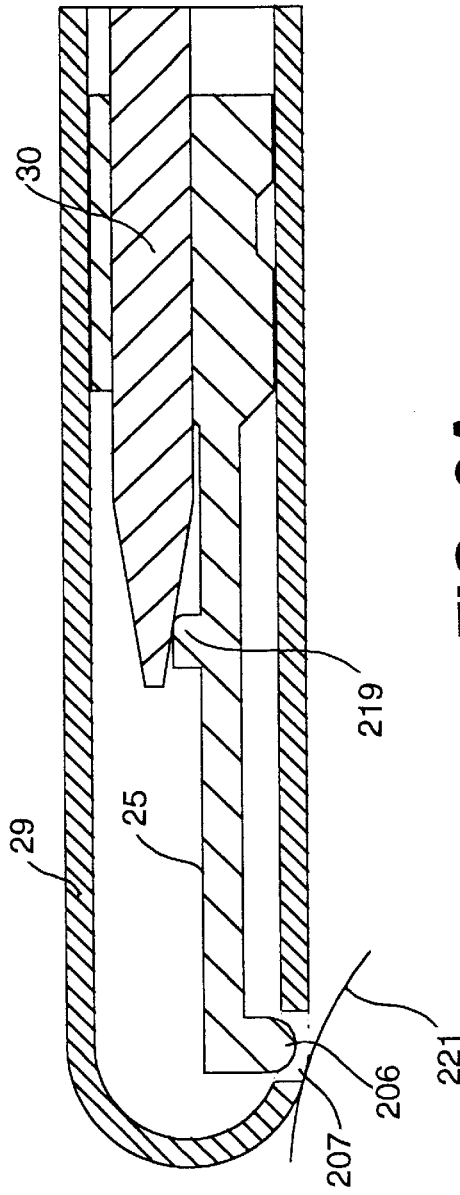
FIG. 9 shows the mechanisms of the loading system during operation. 9A shows the loading system before activation, 9B shows the loading system during measurement.
Figure 9B:
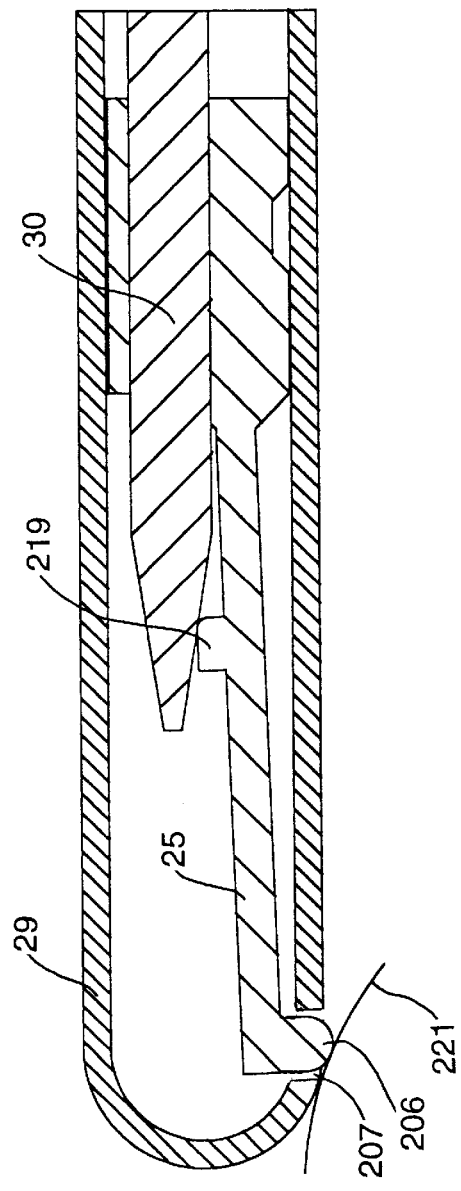

FIG. 9 shows the preferred force detection system during an indenting step. FIG. 9A shows the device in neutral position when not activated. When the device is activated, drive shaft 30 slides against ridge 219, causing sensing arm 25 to flex downward, which in turn extends indenting tip 206 through indenting hole 207 in the distal end of the outer shaft 29 and against the material specimen 221. The portion of sensing arm 25 between ridge 219 and indenting tip 206 flexes as the indenting tip 206 encounters resistance from the material specimen 221. The degree of said flexion is measured by one or more strain gauges 27 (not shown, see FIGS. 8A and 8B) located on the upper and/or lower surfaces of the sensing arm 25. After the above steps are completed, the force detection system is in the position shown in FIG. 9B.

The force detection system may alternatively be a different system known to the art. A mechanical system to measure the beam deflection and then convert it to an electrical signal for processing by any means known to the art including but not limited to a potentiometer whose resistance is varied by the mechanical system. Other systems could also be used which include, but are not limited to, systems utilizing a light source, including but not limited to, laser, infrared, or fiber optics to measure the amount of beam deflection or surface indentation for calculating the stiffness of the material. Another suitable system comprises mounting the indenting tip 206 on a piston head and mounting a pressure sensor within a piston opposite said piston head inside the outer shaft 29. As the indenting tip was pressed against the material, the piston would compress and the pressure sensor would sense the difference in pressure within the piston.

Figure 20:
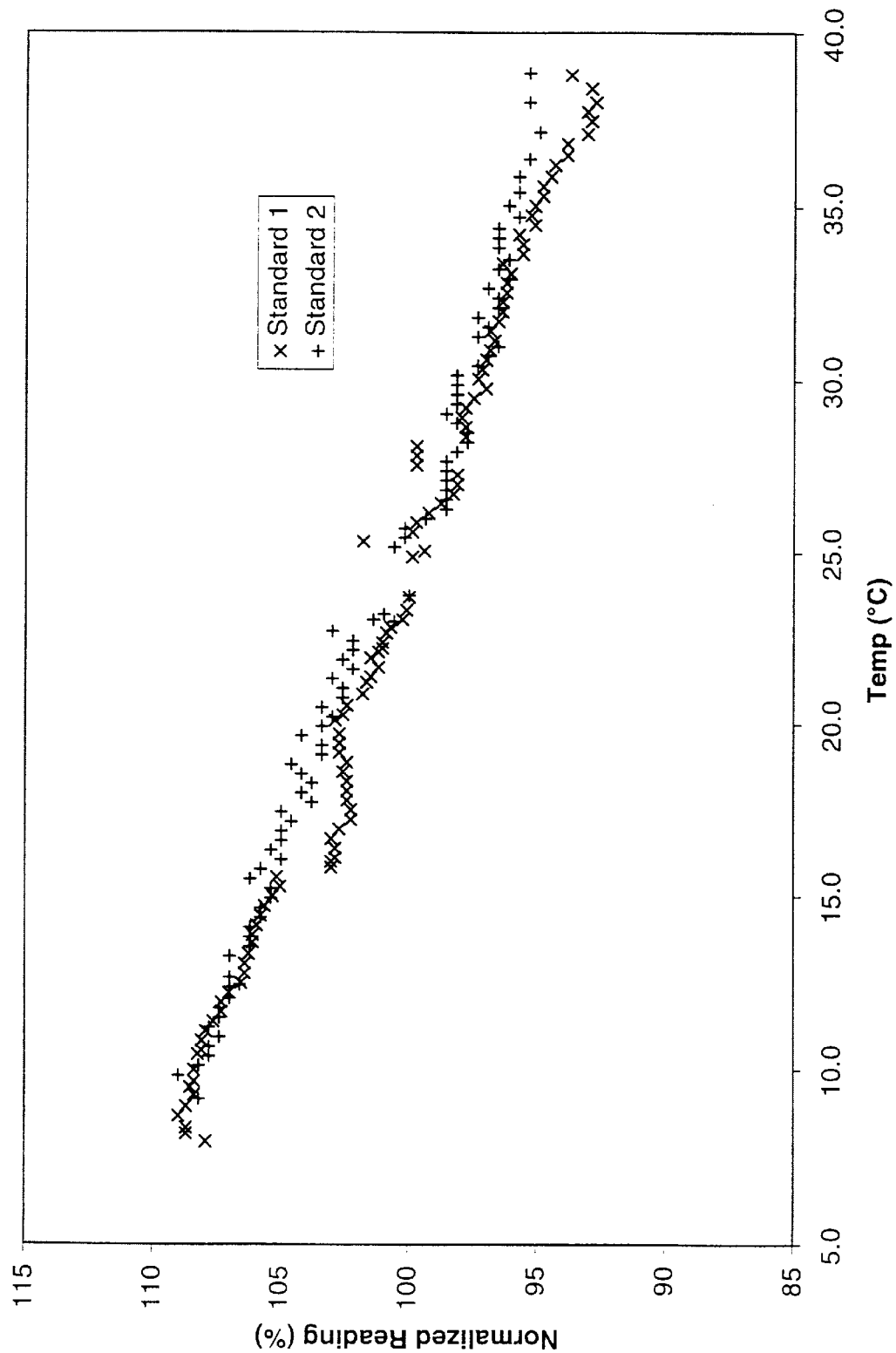
FIG. 20 is a graph showing the effectiveness of a preferred temperature compensation system when tested wet over a wide temperature range for two material standards with drastically different compressibilities.

In the preferred embodiment, semi-conductor strain gauges with temperature compensation circuitry have been found to provide accurate measurements in a temperature range from about 10° C. to about 38° C. being most accurate between about 16° C. and about 32° C. (FIG. 20). The temperature compensation system may also be any system, active or passive, known to the art that would allow the device to measure at different temperatures without significant error and need not be part of the force detection system.

Figure 10:
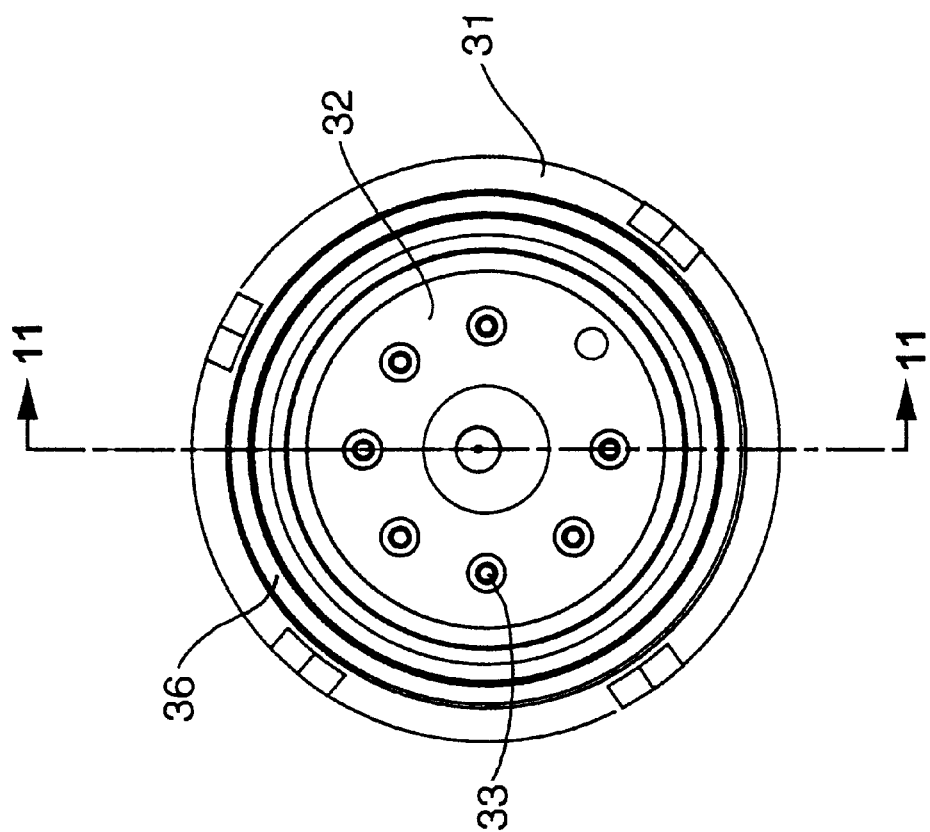
FIG. 10 shows a rear view of the probe.

FIG. 10 shows a rear view of the probe's connecting base 31 comprising probe contact holder 32, probe electrical contacts 33 and probe O-ring 36.

Figure 11:
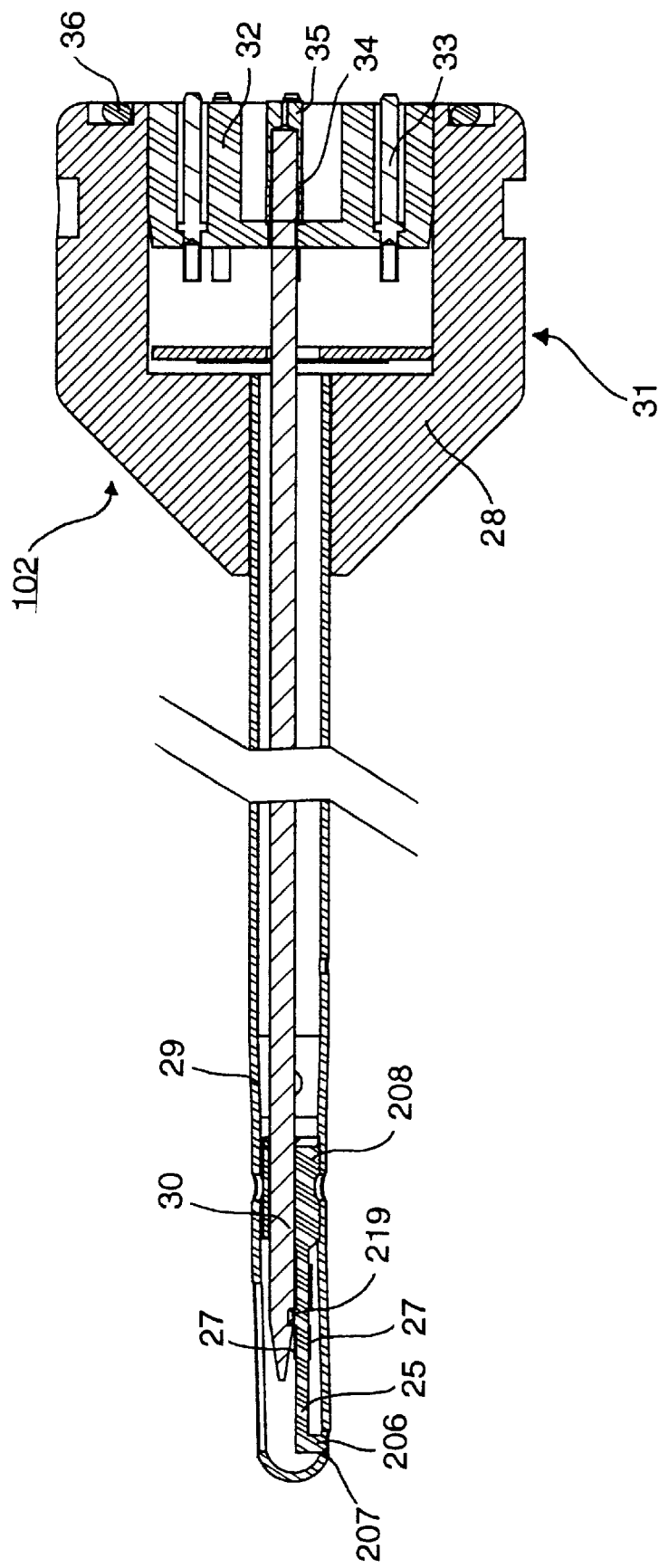
FIG. 11 shows a longitudinal cross-section along line 11—11 of FIG. 10 of the probe with all its components in place. Wiring is not shown.

FIG. 11 is a cross section of probe 102 along line 11—11 of FIG. 10, showing details of the preferred force detection system. The outer shaft 29 is securely attached to the connecting base 31 using any method known to the art. Preferably the flat end of the outer shaft 29 is flush with the inner wall of the connecting base 31. The sensing arm 25 is preferably rigidly attached to the outer shaft 29 at attachment point 208 by any method known to the art. The attachment allows the sensing arm 25 to bend when the drive shaft 30 is moved, pushing the indenting tip 206 through the indenting hole 207. A probe electronics module 28 rests against the inside surface of the connecting base 31. The probe electronics module 28 contains electronics to convert output from the strain gauges 27 to a force measurement and preferably a bridge circuit to balance the raw force signal as well as temperature compensation circuitry for the strain gauges 27. The probe contact holder 32 is press-fitted into the connecting base 31 and secured for a watertight seal. The probe contact holder 32 further contains probe electrical contacts 33 positioned so that when the probe 102 is connected with the handpiece, the probe contact holder 32 is in electrical connection with the handpiece contact holder. Retainer cap 35 is securely attached to the drive shaft 30 to retain a spring 34 mounted on the drive shaft 30 and sitting inside probe contact holder 32. When the drive shaft is moved forward by the action of the motor, spring 34 gets compressed between the face of the probe contact holder 32 and the retainer cap 35. When the motor retracts, spring 34 returns to its initial length, retracting the drive shaft 30.

Preferably, drive shaft 30 extends nearly the entire length of probe 102, through holes in the probe contact holder 32, the probe electronics module 28 and the attachment point 208 of the sensing arm 25.

Figure 12:
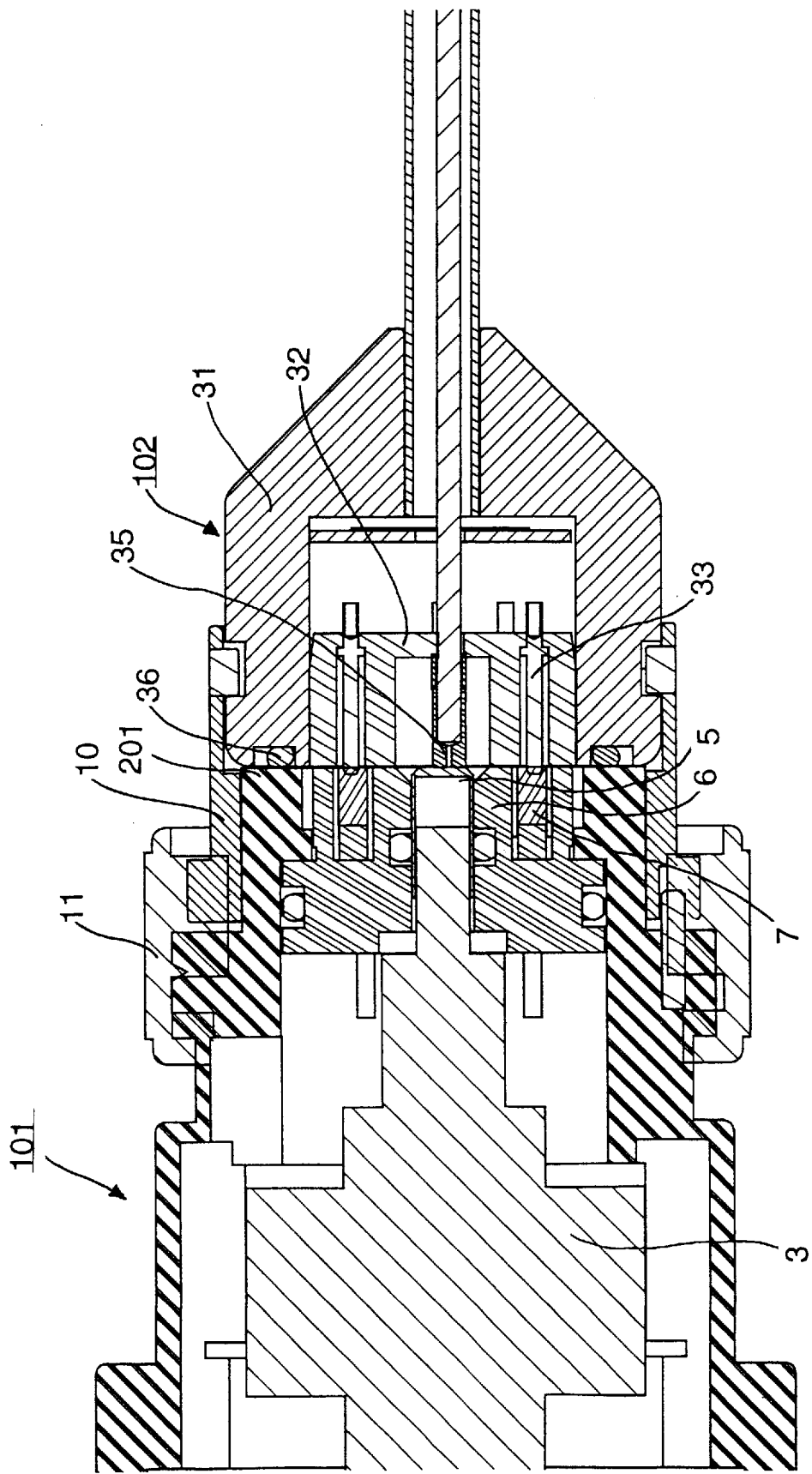
FIG. 12 shows a longitudinal section of part of the device including the connection between the probe and the handpiece when the device is ready for use.

FIG. 12 shows detail of the probe 102 and handpiece 101 when connected. The probe contact holder 32 and the handpiece contact holder 6 are flush against each other. The probe electrical contacts 33 and the handpiece electrical contacts 7 are connected allowing electricity to pass between them. The connecting base 31 has structures which allow it to securely attach to the coupler ring 10. In the preferred embodiment this is a bayonet-type coupler where pins on the coupler ring 10 are slid into pathways along the length of the connecting base 31. The probe 102 is then rolled relative to the handpiece 101, positioning the pins so that the probe 102 cannot move away from the handpiece 101. Other types of connectors known to the art can also be used including but not limited to, pin connectors, screw connectors, or adhesive connectors. To insure a good seal, tightener 11 is screwed down over coupler ring 10 with connecting base 31 in place. Tightener 11 does not allow probe 102 to move, thereby providing a locking seal, and also presses the probe O-ring 36 securely into the housing face 201 of the handpiece contact holder 6 creating a watertight seal between the probe 102 and the handpiece 101.

Alternatively, the probe 102 could be connected to the handpiece 101 is such a way that the probe 102 could be rotated around its main axis while maintaining the position of the handpiece 101. This design would provide the user with additional flexibility to maneuver the indenting tip 206 into hard-to-reach areas, especially when testing body tissues in situ. Such a design would require the electrical contacts between the probe 102 and the handpiece 101 to use a sliding contact system (not shown) such as, but not limited to, a cylindrical slip ring assembly.

Figure 13A:
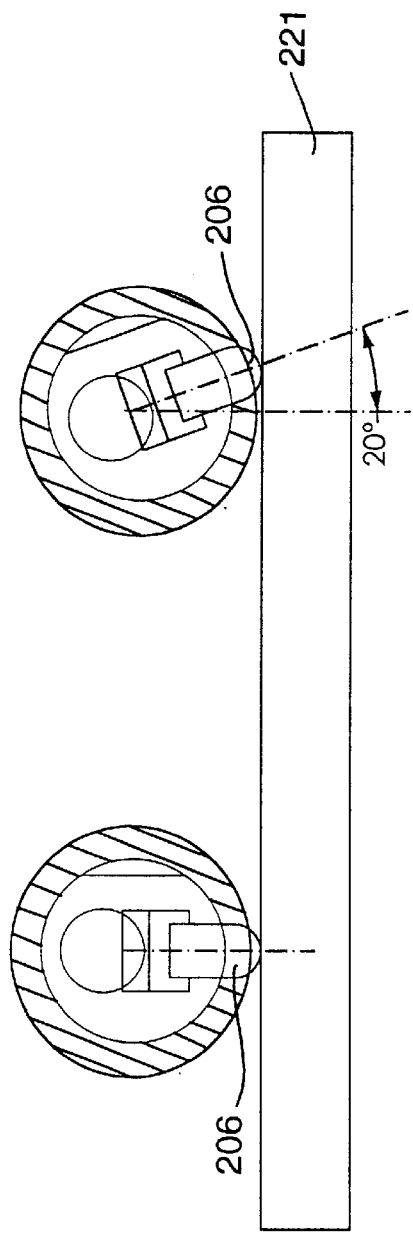
FIG. 13A shows a front view of the convex indenting tip providing variable angle compensation for roll tilting.
Figure 13B:
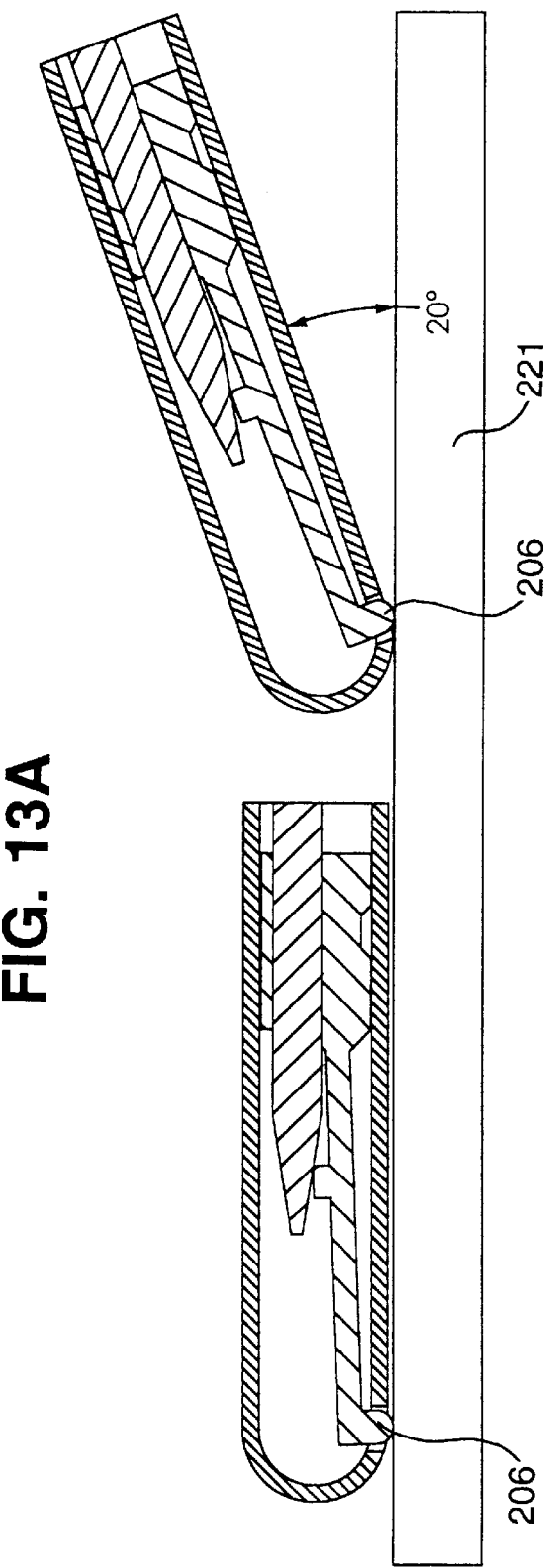
FIG. 13B shows a side view of the device having a convex indenting tip providing variable angle compensation for pitch tilting.

FIG. 13 shows a preferred embodiment of the variable angle compensation system comprising the shape of the indenting tip 206. FIG. 13A illustrates as an example that for roll tilting of 0 to 20 degrees, the size of the contact surface between the indenting tip 206 and the material to be tested 221 is very similar, limiting the effect of the misalignment angle (off-perpendicularity) on the force reading. FIG. 13B illustrates the same effect for pitch tilting. Any shape of the tip which compensates for the misalignment angle's effect on both displacement and force reading is recommended. The indenting tip 206 may therefore be of any mathematical convex shape including but not limited to hemispherical, hyperboloid, or paraboloid. A hemispherical shape is preferred with a paraboloid being most preferred.

Figure 14:
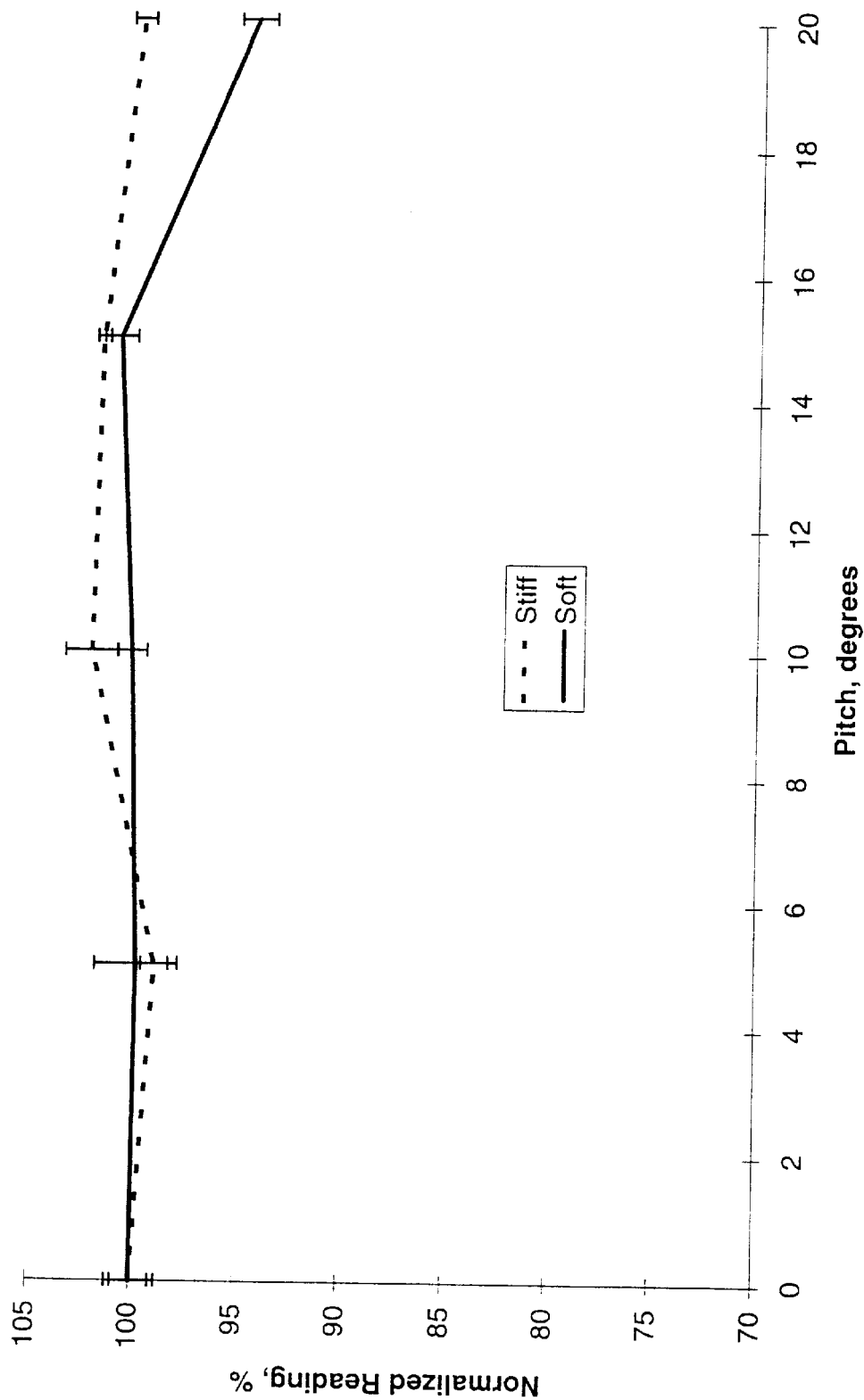
FIG. 14 is a graph showing the effectiveness of the preferred variable angle compensation system on pitch tilting on two material standards with drastically different compressibilities.
Figure 15:
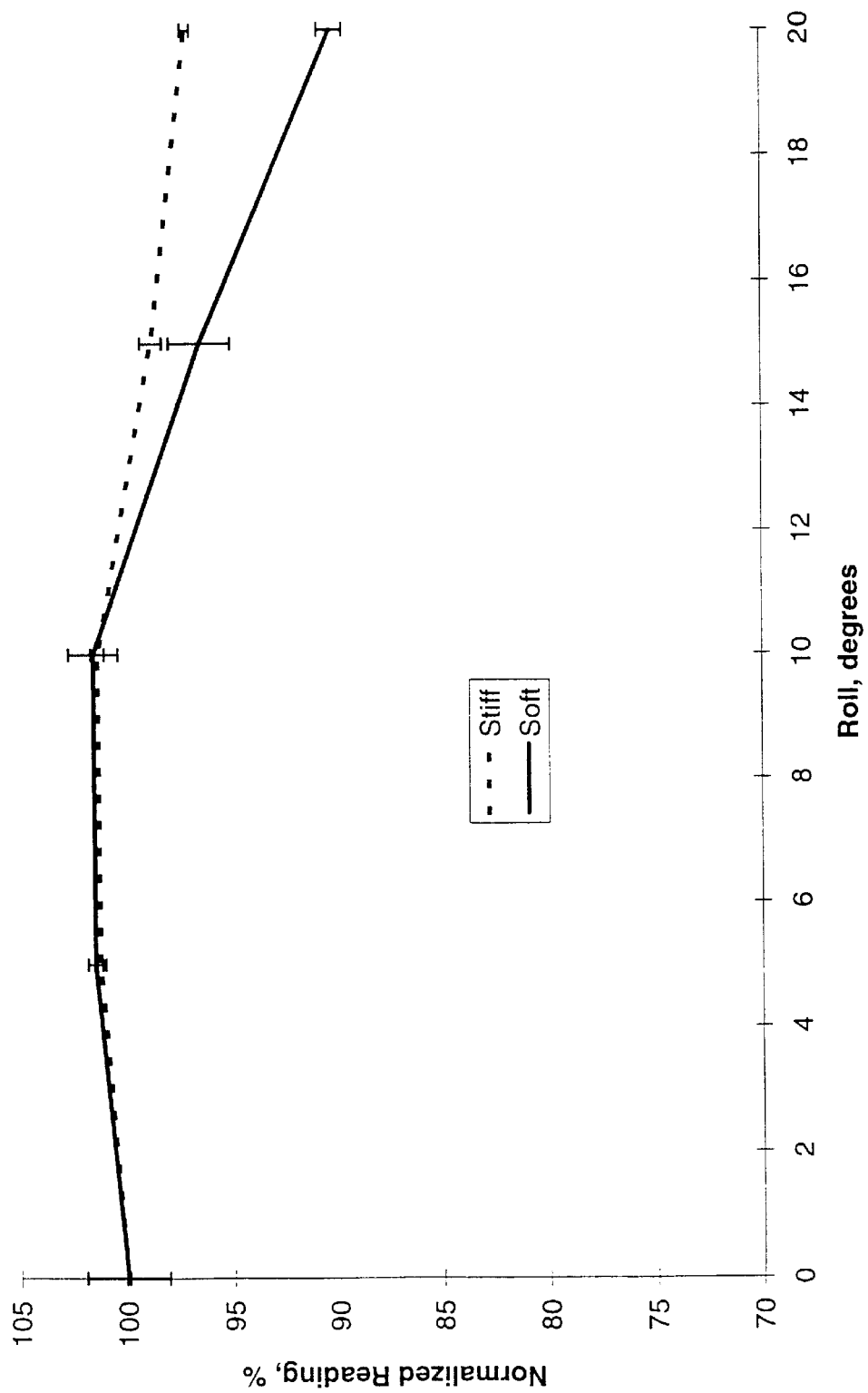
FIG. 15 is a graph showing the effectiveness of the preferred variable angle compensation system on roll tilting on two material standards with drastically different compressibilities.

FIG. 14 shows the effect of pitch on measured results using the device of this invention. FIG. 15 shows the effect of roll on measured results. A tip of hemispherical shape was used for both Figures, and in both tests, both stiff and soft material standards were used. To normalize the results, readings were divided by the average stiffness readings of durometer standards obtained at 0 degrees pitch and roll.

Figure 16:
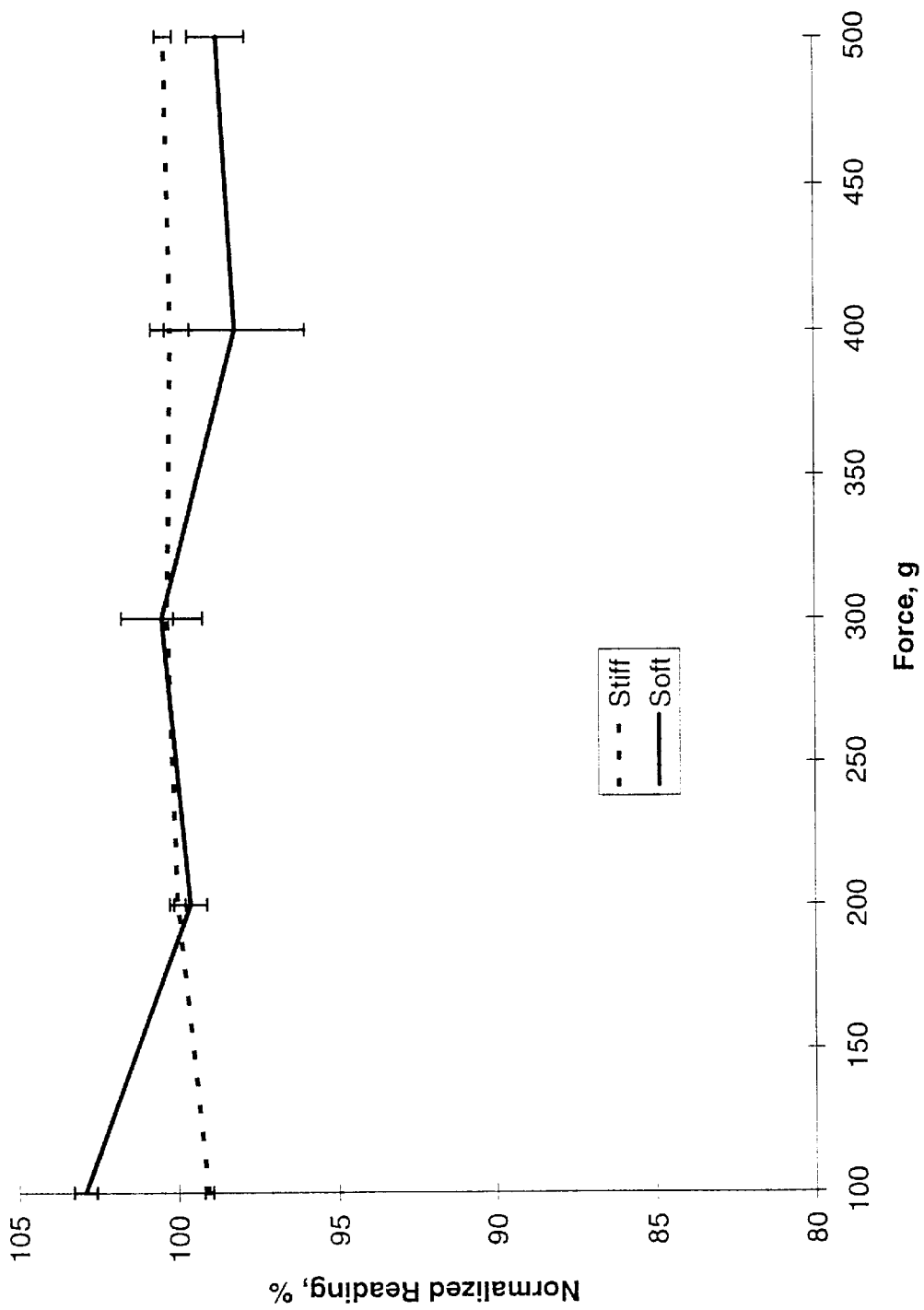
FIG. 16 is a graph showing the effectiveness of the preferred applied force compensation system on two material standards with drastically different compressibilities.

The applied force compensation system could comprise design modifications such as, but not limited to, chamfering of the indentation hole 207 to prevent the material being tested from puckering inside the hole, elevation of the indenting tip 206 within the outer shaft 29, a dedicated strain gauge system of one or more strain gauges and associated electronics to measure any flexion of the outer shaft 29, a drive shaft 30 constructed so as to prevent it from significant flexion either through reinforcement or additional structures, or an indenting step of extremely short duration to limit any applied force effects. In the preferred embodiment the applied force compensation system comprises mechanical support to the drive shaft 30 and chamfering of the indention hole 207. The effectiveness of this system is shown for two material standards of significantly different stiffness in FIG. 16.

Figure 17:
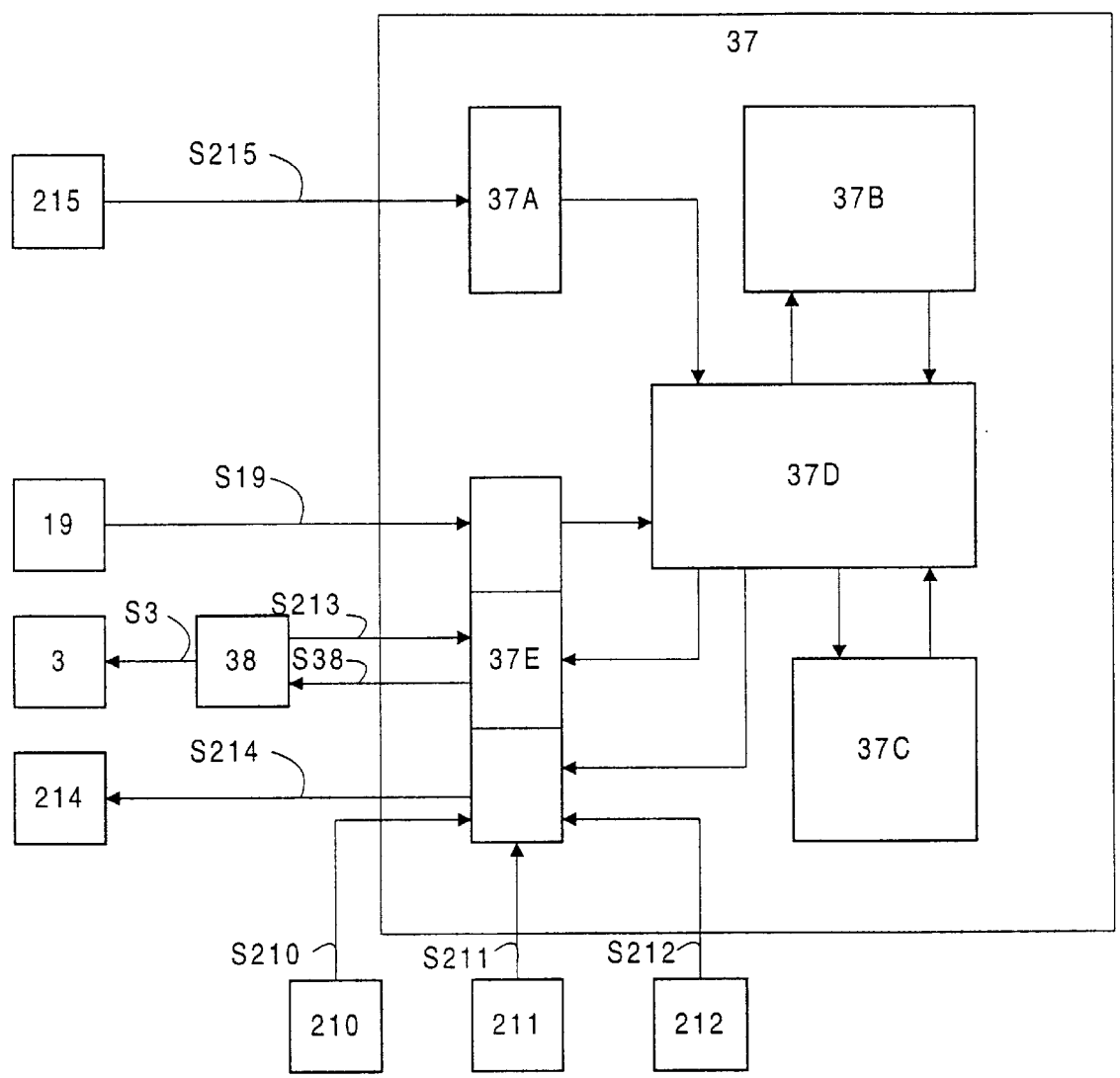
FIG. 17 is a block diagram of the electrical system.

FIG. 17 shows a block layout of the preferred embodiment of the processor 37 as well as the electrical system. Processor 37 is an electrical circuit comprising an analog-to digital converter (ADC) 37A to convert any received analog signals to digital for processing; non-volatile memory 37B, most preferably programmable read-only memory (PROM) to hold a software program and program constants; volatile memory 37C, preferably random access memory (RAM), to hold program variables, a central processing unit (CPU) 37D to run the program stored in PROM 37B and perform calculations as required; and digital input/output (digital I/O) ports 37E to receive signals from and supply signals to the rest of the electronics system. Most preferably the processor 37 contains about 32 kilobytes of PROM and about 512 bytes of RAM. Other processing circuits as known to the art may alternatively be utilized.

The operator places the indenting tip of the device against the material to be tested. When the operator activates switch 19, switch 19 supplies test activation signal S19 to the processor 37 via digital input/output port 37E. Processor 37 then sends out via motor control signal S38 to motor drive circuit 38 a command to move a certain linear distance. The motor drive circuit 38 then converts the motor control signal S38 into motor drive signal S3. The motor 3 receiving the motor drive signal S3 then begins to displace the drive shaft 30 (see FIG. 7). Drive shaft 30 contacts ridge 219 on the sensing arm 25 forcing indenting tip 206 to extend from the head of outer shaft 29 at indenting hole 207 and indent the material specimen 221 (see FIG. 9). In the preferred embodiment, the indentation of the material specimen 221 comprises a set number of motor steps after the device detects contact with the material specimen 221. Most preferably the indenting tip 206 extends no more than about 100 μm into the material specimen 221 after force detection signal 215 indicates force being applied against the tip. The force detection system 215 measures the force being exerted on indenting tip 206 (see FIG. 8) and supplies raw force signal S215 to processor 37. Processor 37 then uses the raw force signal S215 in addition to a distance signal S213 to calculate the stiffness. There need not be an independent distance signal S213. The distance traveled by the indenting tip can be calculated by using a memory in volatile memory 37C of the motor control signals S38 previously sent, preferably a memory record indicating the number of steps after surface detection; or a separate signal on a feedback loop such as that measured using a linear voltage displacement transducer (LVDT), a magnetic position sensor, or a potentiometer and associated circuitry may be used to record the displacement of the drive shaft.

If active compensation systems are used, as opposed to the preferred passive methods, the processor 37 also receives one or more of the following. An angle signal S210 from variable angle compensation system 210, a temperature signal S211 from temperature compensation system 211, and an applied force signal S212 from applied force compensation system 212. These signals are all utilized by processor 37 in addition to distance signal S213 and raw force signal S215 to compensate for the appropriate variables in the calculation of stiffness. After calculating the stiffness, processor 37 then sends rendering signal S214 to rendering system 214 which displays the stiffness on display 14 and signals the user via speaker 216 (FIG. 3).

If errors should occur in measurement due to damage to the probe 102, failure of the power system 23, or other errors predetermined by the manufacturer, the rendering system 214 will display an error message on display 14 and/or an audio signal via speaker 216 instead of or in addition to the computed stiffness. A measurement cycle is completed when one of two alternatives occurs; either the drive shaft 30 has extended to at least a preset distance, or the indenting tip is no longer extending due to its contact with a highly rigid material such as bone. After completion of the measurement cycle, the motor 3 reverses and the drive shaft is returned to its original starting position. In the preferred embodiment this is done by the motor 3 retracting the same number of steps it has moved out and spring 34 using returning force to keep drive shaft 30 in contact with interface button 5. Alternatively any type of method known to the art could be employed which provides for drive shaft 30 returning to its original starting position, including, but not limited to, proximity switches or position sensors.

All necessary power to generate electrical signals, operate electric circuits, or power motor 3 is generated by power system 23 which is regulated by appropriate structures on handle electronics module 21 to insure smooth operation without electrical spikes. In the preferred embodiment, the electrical system is entirely contained within the device's handpiece and probe although, alternatively, the electrical system could be arranged utilizing a mixture of internal circuit boards and external components or additional external support devices including but not limited to displays, input devices, printers, or storage.

Figure 18:
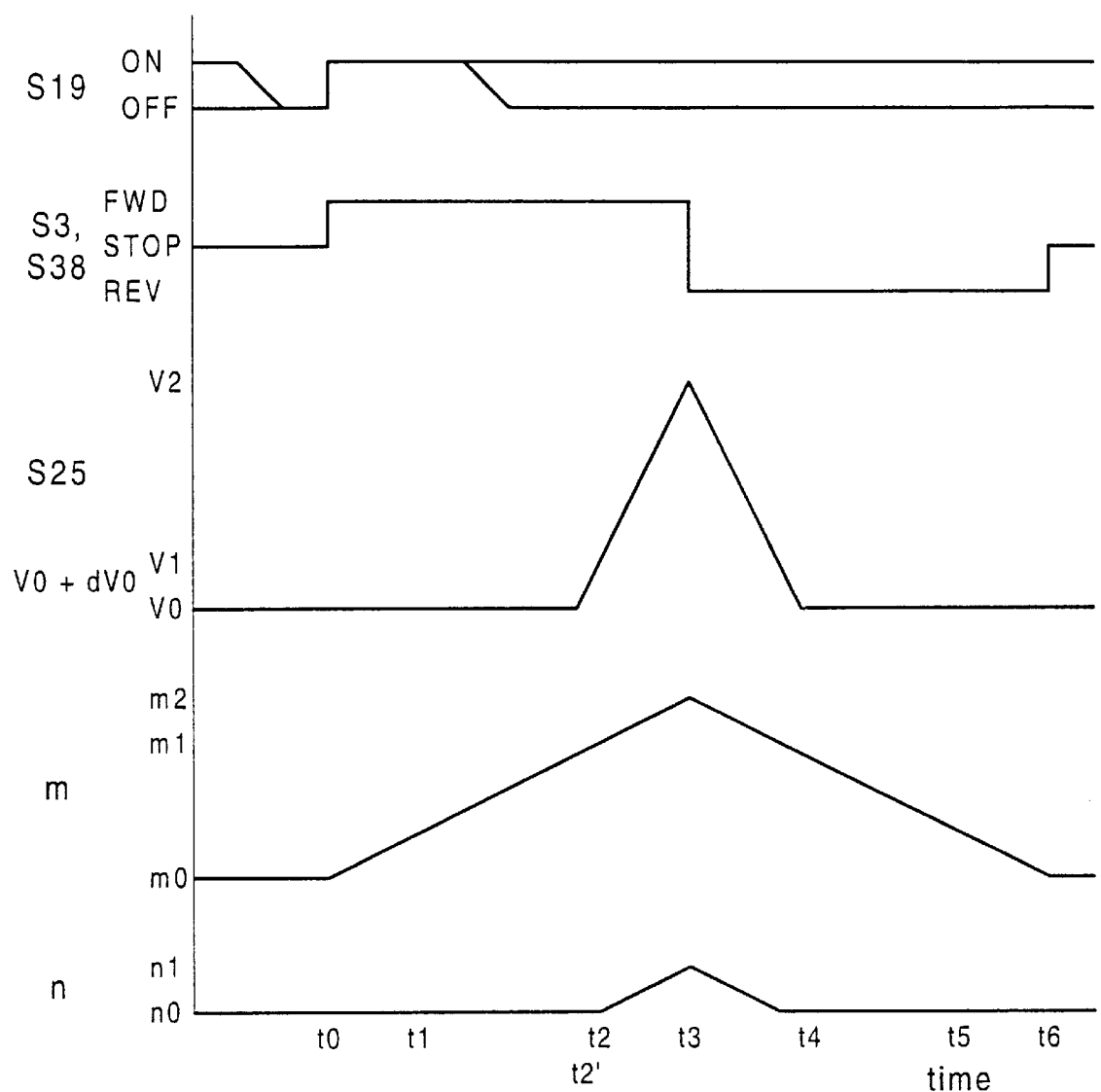
FIG. 18 indicates the signal levels during a single measurement of the device.

FIG. 18 shows signal levels of the device over time. When the user activates switch 19 (FIG. 3) at t0, the test activation signal S19 becomes active and both motor control signal S38 and motor drive signal S3 order the motor to move forward. The total number of motor steps taken, m, begins to be recorded at this time.

At t2' the indenting tip contacts the material to be tested and raw force signal S215 begins.

At t2 the indentation begins, raw force signal S215 rises to V1, and the device begins recording the number of steps taken to indent the material, as well as the raw force signal's S215 rise from V1 to V2.

At t3 the device has completed its forward movement since n1 steps indenting the material (a preset number of steps) have been taken, or raw force signal S215 has reached a preset maximum value V2 indicating contract with a rigid material. At this point, the total number of steps taken, m, has reached m2. Note that the number of steps taken by the motor, m, is greater than the number of steps, n, indenting the material. In fact, n1−n0=m2−m1. The raw force signal S215 now sends the value V2 indicating the maximum force detected. Finally, S38 and S3 command the motor to reverse.

At t4 the indenting tip is no longer in contact with the material's surface but the device has not fully reset to its original starting conditions.

At t6 the total number of steps taken, m, has returned to its original value, m0, so the motor has returned to its original position. S3 and S38 thus command the motor to stop and the device is now reset in preparation of a new measurement.

Experimental results

Clinical studies were performed on human resected knee articular cartilage. A total of 19 patients scheduled for a total knee joint replacement participated in the study. Patients were of both genders, with ages varying from 56 to 84 years old. Testing of the knee joint surfaces, distal femur, proximal tibia, and patella when available, was performed immediately after resection from the patient. Each test site was tested with the device under two conditions to simulate open joint and arthroscopic settings: non-submerged (in air), NS, and submerged in saline, S. Prior to measuring the stiffness of the joint surface, the device output was verified under both conditions using a range of durometer standards. For each site, at least three measurements were obtained to ensure reproducibility. Following the stiffness measurements, the orthopedic surgeon qualitatively evaluated each test site using a nerve hook probe and visual observations by giving a score of I to IV based on the Outerbridge classification system (O.S.). During the entire testing period, the tissue was kept moist with saline. Data was statistically analyzed to determine significant differences.

Figure 19:
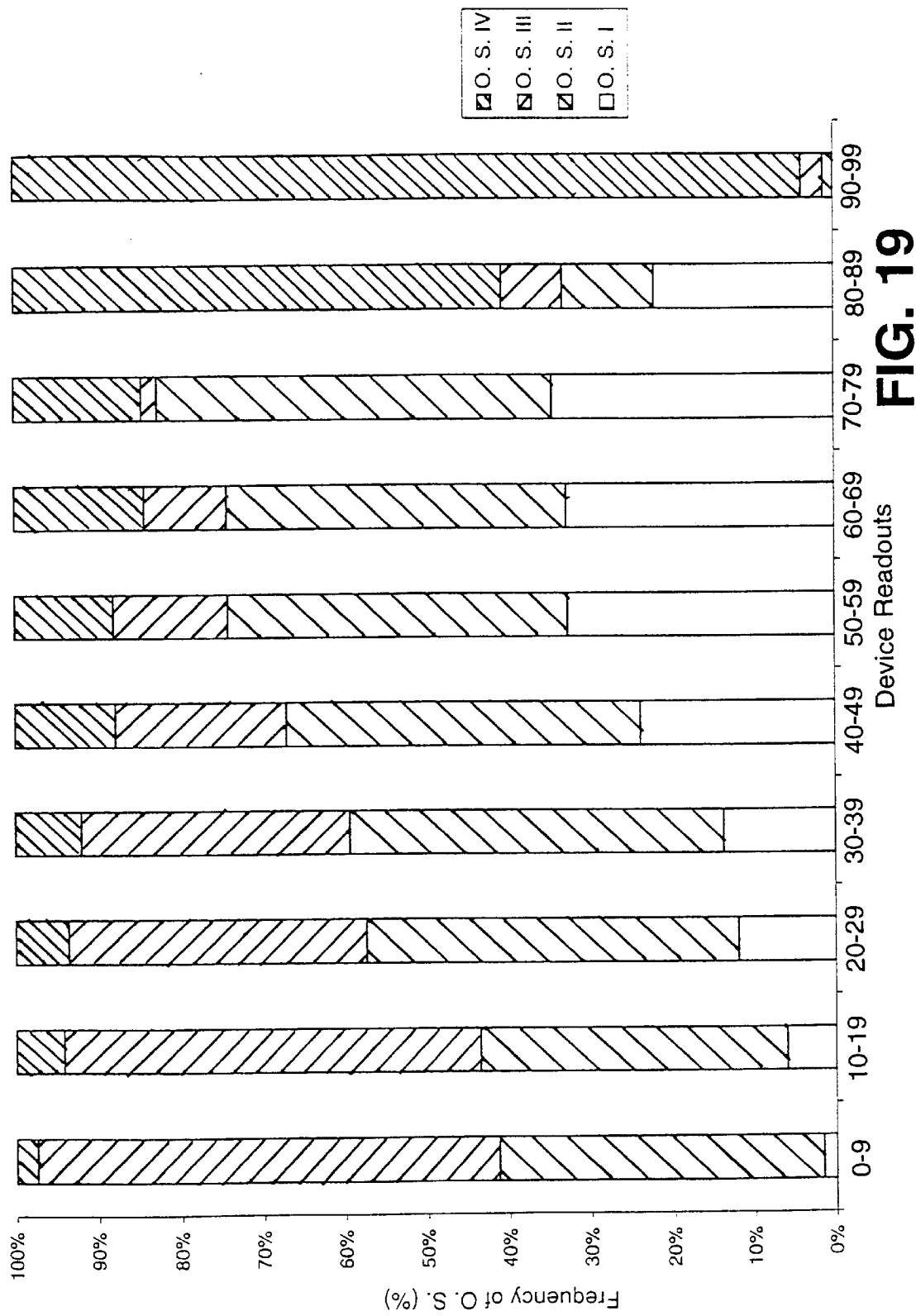
FIG. 19 is a graph plotting the frequency of the various Outerbridge Scores (O.S.) versus the stiffness readouts (grouped in ranges of 10) from the instant device.

As shown in Table 1, prior to each clinical case, verification of the device using the durometer standards indicated that for both non-submerged and submerged conditions mean stiffness values were within 10% of the mean stiffness values of the standards. FIG. 19 shows the graph plotting the frequency of the various Outerbridge Score (O.S.) versus the stiffness readouts (grouped in ranges of 10) from the device. Results indicate that the device readouts correspond well with the condition of the cartilage. For example, for stiffness measurements between 50–80, indicative of stiffer and healthier cartilage, about 75% of the sites were graded O.S. I and II. For stiffness measurements between 0–30, indicative of softer degenerated cartilage, about 48% of the sites were graded with an O.S. III. For stiffness measurements in the 90's, 96% of the sites were graded with an O.S. IV, indicative of cartilage having eroded down to bone.

TABLE 1

Verification of the device using durometer standards:

| Durometer Range | Calibrated Standard | Device (NS) | Device (S) |
| --- | --- | --- | --- |
| blue | 35 | 35 ± 3.1 | 35 ± 3.1 |
| yellow | 55 | 57 ± 6.5 | 62 ± 4.1 |
| black | 81 | 75 ± 5.3 | 81 ± 5.8 |

The results indicate that during clinical evaluation of surface joints, the device subject of the present invention may give the orthopedic surgeon critical information about cartilage degeneration which may not be visible. This is evidenced by the lower stiffness measurements which had been scored as an O.S. I, visually intact cartilage.

Although the description above contains many specificities, these should not be construed as limiting the scope of the invention but merely providing illustrations of some of the presently-preferred embodiments of this invention. Thus the scope of the invention should be determined by the appended claims and their legal equivalents, rather than by the examples given.

We claim:

1. A device for measuring a compressive property of a material comprising:
   a) an indenting tip;
   b) a loading system capable of moving a certain linear distance and pushing said indenting tip into said material;
   c) a force detection system for measuring force exerted on said indenting tip by said material;
   d) a variable angle compensation system for compensating for the effects of tilt of the indenting tip on the force detected by said force detection system; and
   e) a rendering system for converting output of said force detection system to a display representative of said compressive property.

2. A device of claim 1 wherein said variable angle compensation system comprises a convex indenting surface on said indenting tip.

3. A device of claim 2 wherein said indenting surface is a hemisphere.

4. A device of claim 2 wherein said indenting surface is a paraboloid.

5. A device of claim 1, further comprising a temperature compensation system.

6. A device of claim 5 wherein said temperature compensation system comprises one or more strain gauges with associated circuitry for temperature compensation whereby said device is able to measure stiffness at a range of temperatures without significant error.

7. A device of claim 1 further comprising an applied force compensation system.

8. A device of claim 7 wherein said applied force compensation system comprises a chamfered indentation hole and a drive shaft mechanically prevented from flexing.

9. A device of claim 7 wherein said applied force compensation system comprises one or more dedicated strain gauges and associated circuitry.

10. A device of claim 1 wherein said device comprises a handpiece and a probe.

11. A device of claim 10 wherein said probe comprises a structure limiting it to single use.

12. A device of claim 1 wherein said device comprises rechargeable batteries.

13. A device of claim 1 wherein said device comprises disposable batteries.

14. A device of claim 1 which is watertight.

15. A device of claim 1 wherein:
   a) said loading system comprises:
      1) a motor;
      2) a drive shaft moved by said motor; and
      3) a system for determining the movement of said drive shaft;
   b) said force detection system comprises:
      1) a sensing arm solidly connected to said indenting tip; and
      2) one or more strain gauges for measuring the flexion of said sensing arm;
   c) said variable angle compensation system comprises a convex indenting surface on the end of said indenting tip; and
   d) said rendering system comprises a visual display.

16. A method for determining the health or disease of cartilage using a device of claim 1 comprising:
   a) determining a compressive property of said cartilage;
   b) interpolating from said compressive property a measure of health or disease by comparing said compressive property to known measurements of said compressive property of cartilage in established states of health or disease.

17. A watertight device for measuring stiffness of a material comprising:
   a) a handpiece and a probe connected to said handpiece through the use of a bayonet type coupler;
   b) batteries disposed within said handpiece;
   c) an indenting tip made of a rigid material and having a convex tip contoured as a hemisphere or a paraboloid;
   d) a loading system operatively connected to said tip comprising:
      1) a microprocessor-controlled linear actuator capable of step-wise movement;
      2) a drive shaft assembly moved by said linear actuator; and
      3) means operatively connected to said linear actuator for determining the number of steps taken by said linear actuator;
   e) a force detection system comprising:
      1) a sensing arm solidly connected to said indenting tip; and
      2) one or more strain gauges to measure the bend of said sensing arm;
   f) a rendering system operatively connected to said force detection system comprising a liquid crystal display (LCD) capable of providing measurement data, error feedback, low battery, and battery exhausted displays.

18. A method for determining a compressive property of a material comprising:
   a) positioning a device comprising an indenting tip such that said indenting tip contacts said material and means for compensating for effects of angle of contact between said indenting tip and said material;
   b) extending said indenting tip into said material;
   c) measuring force exerted by said material on said indenting tip;
   d) computing the stiffness of said material as a function of said force measurement.

19. A method of claim 18 wherein said material comprises articular cartilage in situ.

* * * * *